(12) United States Patent
Tahmasebi et al.

(10) Patent No.: US 10,426,572 B2
(45) Date of Patent: Oct. 1, 2019

(54) DENTAL TOOL AND GUIDANCE DEVICES

(71) Applicant: Viax Dental Technologies LLC, Hallandale Beach, FL (US)

(72) Inventors: Cyrus Tahmasebi, San Diego, CA (US); Charles Stapleton, Indian Rocks Beach, FL (US)

(73) Assignee: Viax Dental Technologies LLC, Hallandale Beach, FL (US)

( * ) Notice: Subject to any disclaimer, the term of this patent is extended or adjusted under 35 U.S.C. 154(b) by 0 days.

(21) Appl. No.: 15/449,144

(22) Filed: Mar. 3, 2017

(65) Prior Publication Data

US 2017/0172702 A1 Jun. 22, 2017

Related U.S. Application Data

(63) Continuation of application No. 14/119,666, filed as application No. PCT/US2012/039569 on May 25, 2012.

(60) Provisional application No. 61/490,361, filed on May 26, 2011.

(51) Int. Cl.
*A61C 1/08* (2006.01)

(52) U.S. Cl.
CPC .................................. *A61C 1/082* (2013.01)

(58) Field of Classification Search
CPC ......... A61C 1/082; A61C 1/085; A61C 1/084; A61C 3/02
See application file for complete search history.

(56) References Cited

U.S. PATENT DOCUMENTS

| 472,004 A | 3/1892 | Sweet |
| 1,407,840 A | 2/1922 | Cruttenden |
| 1,772,027 A | 8/1930 | Baumgarten |
| 2,303,475 A | 12/1942 | Karlstrom |
| 2,591,183 A | 4/1952 | Mintz |
| 2,597,661 A | 5/1952 | McPhee |

(Continued)

FOREIGN PATENT DOCUMENTS

| AT | 12407 B | 7/1903 |
| AT | 13375 B | 9/1903 |

(Continued)

OTHER PUBLICATIONS

Machine translation of WO 2009/000505 retreived from https://patentscope.wipo.int/search/en/detail.jsf?docId=WO2009000505&recNum=1&maxRec=&office=&prevFilter=&sortOption=&queryString=&tab=PCTDescription on Sep. 11, 2017.*

(Continued)

*Primary Examiner* — Heidi M. Eide
(74) *Attorney, Agent, or Firm* — Lerner, David, Littenberg, Krumholz & Mentlik, LLP

(57) ABSTRACT

The present invention is directed to a system of devices and a method for preparing a tooth to receive a restoration. The system includes a dental instrument for removal of portions of a tooth in the mouth of a patent and an overlay for guiding the dental instrument during the step of tooth removal. The overlay is designed for temporary installation into the mouth of the patient to guide the dental instrument to remove tooth material. The overlay has one or more sets of guide walls, with a predetermined configuration capable of contacting one or more guide projections of the dental instrument, and a receptacle capable of receiving and attaching to the dental instrument.

19 Claims, 17 Drawing Sheets

(56) References Cited

U.S. PATENT DOCUMENTS

| | | |
|---|---|---|
| 2,621,408 A | 12/1952 | Klein |
| 2,634,501 A | 4/1953 | Linet |
| 2,644,235 A | 7/1953 | Mintz |
| 2,675,615 A | 4/1954 | Rosenberg |
| 2,770,040 A | 11/1956 | Moyer |
| 2,986,816 A | 6/1961 | Zeman |
| 3,011,259 A | 12/1961 | Baum |
| 3,063,149 A | 11/1962 | Suga |
| 3,254,413 A | 6/1966 | Suga |
| 3,376,643 A | 4/1968 | Nealon |
| 3,407,503 A | 10/1968 | Nealon |
| 3,445,935 A | 5/1969 | Marshall |
| 3,508,334 A | 4/1970 | Weissman |
| 3,585,723 A | 6/1971 | Simor |
| 3,600,810 A | 8/1971 | Marshall et al. |
| 4,144,645 A | 3/1979 | Marshall |
| 4,226,593 A | 10/1980 | Cohen et al. |
| 4,473,354 A | 9/1984 | Rigaud et al. |
| 4,504,230 A | 3/1985 | Patch |
| 4,526,542 A | 7/1985 | Kochis |
| 4,744,757 A | 5/1988 | Adair et al. |
| 4,778,387 A | 10/1988 | Komatsu |
| 4,941,826 A | 7/1990 | Loran et al. |
| 4,997,369 A | 3/1991 | Shafir |
| 5,015,183 A | 5/1991 | Fenick |
| 5,118,294 A | 6/1992 | Kurer |
| 5,133,660 A | 7/1992 | Fenick |
| 5,135,393 A | 8/1992 | Eidenbenz et al. |
| 5,192,207 A | 3/1993 | Rosellini |
| 5,224,049 A | 6/1993 | Mushabac |
| 5,257,184 A | 10/1993 | Mushabac |
| 5,343,391 A | 8/1994 | Mushabac |
| 5,347,454 A | 9/1994 | Mushabac |
| 5,359,511 A | 10/1994 | Schroeder et al. |
| 5,368,478 A | 11/1994 | Andreiko et al. |
| 5,431,562 A | 7/1995 | Andreiko et al. |
| 5,447,432 A | 9/1995 | Andreiko et al. |
| 5,448,472 A | 9/1995 | Mushabac |
| 5,454,717 A | 10/1995 | Andreiko et al. |
| 5,545,039 A | 8/1996 | Mushabac |
| 5,556,278 A | 9/1996 | Meitner |
| 5,562,448 A | 10/1996 | Mushabac |
| 5,569,578 A | 10/1996 | Mushabac |
| 5,575,646 A | 11/1996 | Giannella |
| 5,575,656 A | 11/1996 | Hajjar |
| 5,641,287 A | 6/1997 | Gittleman |
| 5,725,376 A | 3/1998 | Poirier |
| 5,768,134 A | 6/1998 | Swaelens et al. |
| 5,800,168 A | 9/1998 | Cascione et al. |
| 5,813,859 A | 9/1998 | Hajjar et al. |
| 5,897,315 A | 4/1999 | Nakayama et al. |
| 5,975,893 A | 11/1999 | Chishti et al. |
| 6,030,211 A | 2/2000 | Sandhaus |
| 6,049,743 A | 4/2000 | Baba |
| 6,183,248 B1 | 2/2001 | Chishti et al. |
| 6,190,171 B1 | 2/2001 | Hajjar et al. |
| 6,213,770 B1 | 4/2001 | Kuhn |
| 6,254,639 B1 | 7/2001 | Peckitt |
| 6,257,892 B1 | 7/2001 | Worthington |
| 6,309,215 B1 | 10/2001 | Phan et al. |
| 6,334,853 B1 | 1/2002 | Kopelman et al. |
| 6,371,761 B1 | 4/2002 | Cheang et al. |
| 6,382,975 B1 | 5/2002 | Poirier |
| 6,390,812 B1 | 5/2002 | Chishti et al. |
| 6,398,548 B1 | 6/2002 | Muhammad et al. |
| 6,406,292 B1 | 6/2002 | Chishti et al. |
| 6,447,296 B2 | 9/2002 | Worthington |
| 6,457,972 B1 | 10/2002 | Chishti et al. |
| 6,471,511 B1 | 10/2002 | Chishti et al. |
| 6,485,298 B2 | 11/2002 | Chishti et al. |
| 6,511,323 B1 | 1/2003 | Wilkinson |
| 6,527,550 B1 | 3/2003 | Hajjar et al. |
| 6,537,067 B1 | 3/2003 | Wennemann |
| 6,554,611 B2 | 4/2003 | Chishti et al. |
| 6,626,672 B1 | 9/2003 | Been |
| 6,641,340 B1 | 11/2003 | Hajjar et al. |
| 6,685,469 B2 | 2/2004 | Chishti et al. |
| 6,705,861 B2 | 3/2004 | Chishti et al. |
| 6,722,880 B2 | 4/2004 | Chishti et al. |
| 6,767,208 B2 | 7/2004 | Kaza |
| 6,786,726 B2 | 9/2004 | Lehmann et al. |
| 6,814,575 B2 | 11/2004 | Poirier |
| 6,925,198 B2 | 8/2005 | Scharlack et al. |
| 6,957,118 B2 | 10/2005 | Kopelman et al. |
| 7,004,757 B2 | 2/2006 | Wilkinson |
| 7,059,850 B1 | 6/2006 | Phan et al. |
| 7,097,451 B2 | 8/2006 | Tang |
| 7,108,511 B1 | 9/2006 | Shatkin |
| 7,110,844 B2 | 9/2006 | Kopelman et al. |
| 7,121,825 B2 | 10/2006 | Chishti et al. |
| 7,123,767 B2 | 10/2006 | Jones et al. |
| 7,125,248 B2 | 10/2006 | Phan et al. |
| 7,134,874 B2 | 11/2006 | Chishti et al. |
| 7,140,877 B2 | 11/2006 | Kaza |
| 7,147,465 B2 | 12/2006 | Jung et al. |
| 7,172,424 B2 | 2/2007 | Wu |
| 7,245,977 B1 | 7/2007 | Simkins |
| 7,287,982 B2 | 10/2007 | Riley et al. |
| 7,331,786 B2 | 2/2008 | Poirier |
| 7,346,417 B2 | 3/2008 | Luth et al. |
| 7,357,637 B2 | 4/2008 | Liechtung |
| 7,367,801 B2 | 5/2008 | Saliger |
| 7,377,778 B2 | 5/2008 | Chishti et al. |
| 7,383,094 B2 | 6/2008 | Kopelman et al. |
| 7,384,266 B2 | 6/2008 | Wen |
| 7,393,211 B2 | 7/2008 | Wilkinson |
| 7,442,040 B2 | 10/2008 | Kuo |
| 7,474,307 B2 | 1/2009 | Chishti et al. |
| 7,476,100 B2 | 1/2009 | Kuo |
| 7,536,234 B2 | 5/2009 | Kopelman et al. |
| 7,555,403 B2 | 6/2009 | Kopelman et al. |
| 7,572,125 B2 | 8/2009 | Brajnovic |
| 7,590,462 B2 | 9/2009 | Rubbert et al. |
| 7,653,455 B2 | 1/2010 | Cinader, Jr. |
| 7,658,610 B2 | 2/2010 | Knopp |
| 7,695,281 B2 | 4/2010 | Burger et al. |
| 7,708,557 B2 | 5/2010 | Rubbert |
| 7,734,368 B2 | 6/2010 | Kopelman et al. |
| 7,774,084 B2 | 8/2010 | Cinader, Jr. |
| 7,801,632 B2 | 9/2010 | Orth et al. |
| 7,802,987 B1 | 9/2010 | Phan |
| 7,837,469 B2 | 11/2010 | Chishti et al. |
| 7,845,942 B2 | 12/2010 | Wilkinson |
| 7,854,611 B2 | 12/2010 | Yau et al. |
| 7,862,336 B2 | 1/2011 | Kopelman et al. |
| 7,866,980 B2 | 1/2011 | Poirier |
| 7,905,726 B2 | 3/2011 | Stumpel |
| 7,996,099 B2 | 8/2011 | Kopelman et al. |
| 8,011,927 B2 | 9/2011 | Berckmans, III et al. |
| 8,021,153 B2 | 9/2011 | Poirier |
| 8,038,440 B2 | 10/2011 | Swaelens et al. |
| 8,041,439 B2 | 10/2011 | Kopelman et al. |
| 8,043,091 B2 | 10/2011 | Schmitt |
| 8,099,268 B2 | 1/2012 | Kitching et al. |
| 8,170,327 B2 | 5/2012 | Glor et al. |
| 8,186,999 B2 | 5/2012 | Andersson et al. |
| 8,301,287 B2 | 10/2012 | Kopelman et al. |
| 8,359,114 B2 | 1/2013 | Steingart et al. |
| 8,359,115 B2 | 1/2013 | Kopelman et al. |
| 8,364,301 B2 | 1/2013 | Schmitt |
| 8,398,396 B2 | 3/2013 | Taormina |
| 8,401,686 B2 | 3/2013 | Moss et al. |
| 8,425,973 B2 | 4/2013 | Dunne |
| 8,449,296 B2 | 5/2013 | Liechtung |
| 8,454,362 B2 | 6/2013 | Rubbert |
| 8,454,365 B2 | 6/2013 | Boerjes et al. |
| 8,562,340 B2 | 10/2013 | Chishti et al. |
| 8,602,780 B2 | 12/2013 | Rubbert |
| 8,638,447 B2 | 1/2014 | Babayoff et al. |
| 8,638,448 B2 | 1/2014 | Babayoff et al. |
| 8,640,338 B2 | 2/2014 | Jacquemyns |
| 8,651,859 B2 | 2/2014 | Chishti et al. |
| 8,651,860 B2 | 2/2014 | Kwon |
| 8,714,975 B2 | 5/2014 | Stumpel |

(56) References Cited

U.S. PATENT DOCUMENTS

| | | | |
|---|---|---|---|
| 8,721,329 B2 | 5/2014 | Hultgren et al. |
| 8,734,150 B2 | 5/2014 | Chishti et al. |
| 8,753,114 B2 | 6/2014 | Vuillemot |
| 8,753,118 B2 | 6/2014 | Randall |
| D708,330 S | 7/2014 | Jung |
| 8,770,972 B2 | 7/2014 | Swaelens et al. |
| 8,794,964 B2 | 8/2014 | Haber |
| 8,803,958 B2 | 8/2014 | Zhang et al. |
| 8,807,999 B2 | 8/2014 | Kuo et al. |
| D713,034 S | 9/2014 | Jung |
| 8,828,287 B2 | 9/2014 | van der Zel |
| 8,897,526 B2 | 11/2014 | MacLeod et al. |
| 8,899,984 B2 | 12/2014 | Llop et al. |
| 8,926,327 B2 | 1/2015 | Massad |
| 8,926,328 B2 | 1/2015 | Suttin |
| 8,954,181 B2 | 2/2015 | MacLeod et al. |
| 9,011,147 B2 | 4/2015 | Jacquemyns |
| 9,011,148 B2 | 4/2015 | Dolti et al. |
| 9,044,296 B2 | 6/2015 | Randall |
| 9,069,914 B2 | 6/2015 | Kopelman et al. |
| 9,089,388 B2 | 7/2015 | Zegarelli |
| 9,107,723 B2 | 8/2015 | Hall et al. |
| 9,125,712 B2 | 9/2015 | Kraemer et al. |
| 9,161,824 B2 | 10/2015 | Chishti et al. |
| 9,168,114 B2 | 10/2015 | Jung et al. |
| 9,186,228 B2 | 11/2015 | Kopelman et al. |
| 9,208,531 B2 | 12/2015 | Boerjes et al. |
| 9,220,576 B2 | 12/2015 | Heinz et al. |
| 9,259,291 B2 | 2/2016 | Gantes |
| 9,295,534 B2 | 3/2016 | Ruppert et al. |
| 9,299,192 B2 | 3/2016 | Kopelman |
| 9,320,572 B2 | 4/2016 | Deichmann et al. |
| 9,320,575 B2 | 4/2016 | Chishti et al. |
| 9,411,910 B2 | 8/2016 | Methot |
| 9,519,749 B2 | 12/2016 | Stumpel |
| 9,579,170 B2 | 2/2017 | Van Lierde et al. |
| 9,763,746 B2 | 9/2017 | Deichmann et al. |
| 9,901,416 B2 | 2/2018 | Gantes |
| 9,901,417 B2 | 2/2018 | Gantes |
| 9,931,177 B2 | 4/2018 | Wouters et al. |
| 9,949,807 B2 | 4/2018 | Orth et al. |
| 9,975,294 B2 | 5/2018 | Taub et al. |
| 2001/0036617 A1 | 11/2001 | Karmaker et al. |
| 2002/0015934 A1 | 2/2002 | Rubbert et al. |
| 2002/0160337 A1 | 10/2002 | Klein et al. |
| 2003/0008259 A1 | 1/2003 | Kuo et al. |
| 2003/0064346 A1 | 4/2003 | Wennemann |
| 2004/0043355 A1 | 3/2004 | Jonsson et al. |
| 2004/0091836 A1 | 5/2004 | Lazare |
| 2004/0248065 A1 | 12/2004 | Schneider |
| 2005/0014109 A1 | 1/2005 | Lim |
| 2005/0095554 A1 | 5/2005 | Wilkinson |
| 2005/0244782 A1 | 11/2005 | Chishti et al. |
| 2005/0282106 A1 | 12/2005 | Sussman et al. |
| 2006/0008777 A1 | 1/2006 | Peterson et al. |
| 2006/0127848 A1 | 6/2006 | Sogo et al. |
| 2007/0218423 A1 | 9/2007 | Sapian |
| 2007/0238068 A1 | 10/2007 | Comfortes |
| 2007/0292821 A1 | 12/2007 | De Vreese |
| 2008/0085490 A1 | 4/2008 | Jabri |
| 2008/0153067 A1 | 6/2008 | Berckmans et al. |
| 2008/0176187 A1 | 7/2008 | Stumpel |
| 2008/0227056 A1 | 9/2008 | Bulard |
| 2008/0259411 A1 | 10/2008 | Karlsson |
| 2008/0287953 A1 | 11/2008 | Sers |
| 2008/0312659 A1 | 12/2008 | Metzger et al. |
| 2008/0318187 A1 | 12/2008 | Wilkinson |
| 2009/0004629 A1 | 1/2009 | Fishman et al. |
| 2009/0035720 A1 | 2/2009 | Viscomi |
| 2009/0263764 A1 | 10/2009 | Berckmans, III et al. |
| 2009/0274990 A1 | 11/2009 | Kim |
| 2009/0291417 A1 | 11/2009 | Rubbert et al. |
| 2010/0173259 A1* | 7/2010 | Vogel ............... A61C 1/084 |
| | | 433/72 |
| 2010/0185201 A1 | 7/2010 | Kim |
| 2010/0192375 A1* | 8/2010 | Jacquemyns ........... A61C 3/02 |
| | | 29/896.1 |
| 2010/0196842 A1 | 8/2010 | Jacquemyns |
| 2011/0112544 A1 | 5/2011 | Haber |
| 2011/0245951 A1 | 10/2011 | Gantes |
| 2011/0269104 A1 | 11/2011 | Berckmans, III et al. |
| 2012/0129126 A1 | 5/2012 | Nouriam et al. |
| 2012/0143364 A1* | 6/2012 | Mcleod .................. A61C 1/082 |
| | | 700/98 |
| 2012/0175799 A1 | 7/2012 | Karlsson et al. |
| 2012/0178045 A1 | 7/2012 | Massad |
| 2012/0270176 A1 | 10/2012 | Jacquemyns |
| 2012/0308963 A1 | 12/2012 | Hasselgren et al. |
| 2012/0322025 A1 | 12/2012 | Ozawa et al. |
| 2013/0017507 A1* | 1/2013 | Moffson ................ A61C 1/084 |
| | | 433/27 |
| 2013/0108988 A1 | 5/2013 | Simoncic |
| 2013/0108989 A1 | 5/2013 | Kim |
| 2013/0115573 A1 | 5/2013 | Lampl |
| 2013/0172731 A1 | 7/2013 | Gole |
| 2013/0177864 A1 | 7/2013 | Hultgren et al. |
| 2013/0209953 A1 | 8/2013 | Arlinsky et al. |
| 2013/0224691 A1 | 8/2013 | Liechtung |
| 2013/0244208 A1 | 9/2013 | Rubbert |
| 2013/0277874 A1 | 10/2013 | Johnson et al. |
| 2013/0337412 A1 | 12/2013 | Kwon |
| 2014/0008826 A1 | 1/2014 | Dierkes et al. |
| 2014/0026419 A1 | 1/2014 | Haber |
| 2014/0080093 A1 | 3/2014 | Rubbert |
| 2014/0113251 A1 | 4/2014 | Schweiger et al. |
| 2014/0193769 A1 | 7/2014 | Mackey |
| 2014/0193770 A1 | 7/2014 | Mackey |
| 2014/0193772 A1 | 7/2014 | Mackey |
| 2014/0205968 A1 | 7/2014 | Jung et al. |
| 2014/0215804 A1 | 8/2014 | Jacquemyns |
| 2014/0234804 A1 | 8/2014 | Huang et al. |
| 2014/0242541 A1 | 8/2014 | Jung et al. |
| 2014/0242547 A1 | 8/2014 | Randall |
| 2014/0248577 A1 | 9/2014 | Tahmasebi et al. |
| 2014/0255873 A1 | 9/2014 | Bullis et al. |
| 2014/0277665 A1 | 9/2014 | Fisker |
| 2014/0308623 A1 | 10/2014 | Chang |
| 2014/0315154 A1 | 10/2014 | Jung et al. |
| 2014/0316750 A1 | 10/2014 | Jung et al. |
| 2014/0358497 A1 | 12/2014 | Kuo et al. |
| 2015/0057675 A1 | 2/2015 | Akeel et al. |
| 2015/0150684 A1 | 6/2015 | De Clerck |
| 2015/0182301 A1 | 7/2015 | Hegland |
| 2015/0202028 A1 | 7/2015 | Randall |
| 2015/0216638 A1 | 8/2015 | Baaske et al. |
| 2015/0230894 A1 | 8/2015 | Juzbasic et al. |
| 2015/0250568 A1 | 9/2015 | Fisker et al. |
| 2015/0251405 A1 | 9/2015 | Kopelman et al. |
| 2015/0257853 A1 | 9/2015 | Jacquemyns |
| 2015/0282913 A1 | 10/2015 | Zegarelli |
| 2015/0289954 A1 | 10/2015 | Chang |
| 2015/0302170 A1 | 10/2015 | Berckmans, III et al. |
| 2015/0327967 A1 | 11/2015 | Baaske et al. |
| 2016/0000522 A1 | 1/2016 | Ripoche et al. |
| 2016/0008093 A1 | 1/2016 | Lampl |
| 2016/0030141 A1 | 2/2016 | Kopelman et al. |
| 2016/0074141 A1 | 3/2016 | Lozada |
| 2016/0143716 A1 | 5/2016 | Beyer et al. |
| 2016/0143717 A1 | 5/2016 | Samrano |
| 2016/0157970 A1 | 6/2016 | Gantes |
| 2016/0193019 A1 | 7/2016 | Heinz et al. |

FOREIGN PATENT DOCUMENTS

| | | |
|---|---|---|
| AU | 2002210903 B2 | 2/2006 |
| CN | 1536975 A | 10/2004 |
| CN | 1555247 A | 12/2004 |
| CN | 1678254 A | 10/2005 |
| DE | 3730055 A1 | 3/1989 |
| DE | 4012327 A1 | 10/1991 |
| DE | 19947844 A1 | 4/2001 |
| DE | 102010031018 A1 | 1/2012 |
| DE | 102012003811 A1 | 8/2013 |
| EP | 1547544 A1 | 6/2005 |

(56) References Cited

FOREIGN PATENT DOCUMENTS

| | | |
|---|---|---|
| EP | 2272462 A1 | 1/2011 |
| EP | 2742906 A1 | 6/2014 |
| JP | S63275335 A | 11/1988 |
| JP | H101059113 U | 4/1989 |
| JP | 08010268 | 1/1996 |
| JP | 3114270 U | 10/2005 |
| JP | 2007511275 A | 5/2007 |
| KR | 20030064772 A | 8/2003 |
| KR | 20120053455 A | 5/2012 |
| KR | 20160018156 A | 2/2016 |
| KR | 20160018158 A | 2/2016 |
| KR | 20160056855 A | 5/2016 |
| SU | 1438757 A1 | 11/1988 |
| SU | 1674828 A1 | 9/1991 |
| WO | 9115163 A1 | 10/1991 |
| WO | 9627343 A1 | 9/1996 |
| WO | 0032131 A1 | 6/2000 |
| WO | 0234154 A2 | 5/2002 |
| WO | 2005055852 A2 | 6/2005 |
| WO | 2007104842 A1 | 9/2007 |
| WO | 2007129955 A1 | 11/2007 |
| WO | 2009048475 A1 | 4/2009 |
| WO | 2009073498 A1 | 6/2009 |
| WO | 2009089129 A1 | 7/2009 |
| WO | 2009094576 A1 | 7/2009 |
| WO | 2009105684 A1 | 8/2009 |
| WO | 2011003612 A1 | 1/2011 |
| WO | 2012006717 A1 | 1/2012 |
| WO | 2012076574 A2 | 6/2012 |
| WO | 2012085285 A2 | 6/2012 |
| WO | 2012110850 A2 | 8/2012 |
| WO | 2012162605 A2 | 11/2012 |
| WO | 2012163466 A1 | 12/2012 |
| WO | 2013026600 A1 | 2/2013 |
| WO | 2013181721 A2 | 12/2013 |
| WO | 2014135178 A1 | 9/2014 |
| WO | 2014138643 A2 | 9/2014 |
| WO | 2014198873 A1 | 12/2014 |
| WO | 2016094272 A1 | 6/2016 |

OTHER PUBLICATIONS

International Search Report and Written Opinion for Application No. PCT/US2012/039569 dated Sep. 14, 2012.
Canadian Office Action for Application No. 2,750,698 dated Apr. 10, 2013.
P. Hahn, Fracture strengh of 3-unit inlay bridges after thermo-mechanical fatigue in a chewing simulator, http://www.gapless.de/, Oct. 25, 2001, 2 pages.
Chinese Office Action for Application No. 201080014124.5 dated Sep. 18, 2013.
Japanese Office Action for Application No. 2011-546876 dated Dec. 20, 2013.
Australian Examination Report for Application No. 2010209671 dated Jan. 29, 2014.
Russian Office Action for Application No. 2011136473 dated Feb. 22, 2014.
Mexican Office Action for Application No. MX/a/2011/008128 dated Apr. 9, 2014.
Japanese Office Action for Application No. 2011-546876 dated Aug. 5, 2014.
Mexican Office Action for Application No. MX/a/2011/008128 dated Nov. 11, 2014.
Extended European Search Report for Application No. 12790260.9 dated Jun. 19, 2015.
Search Report for Russian Application No. 2014151779 dated Dec. 20, 2016.
Australian Examination Report for AU2017204455 dated Apr. 18, 2018.
Japanese Office Action for Application No. 2018-004431 dated Jan. 8, 2019.
Japanese Office Action for Application No. 2018-004457 dated Jan. 22, 2019.

* cited by examiner

US 10,426,572 B2

DENTAL TOOL AND GUIDANCE DEVICES

CROSS-REFERENCE TO RELATED APPLICATION

The present application is a continuation of U.S. patent application Ser. No. 14/119,666 filed Mar. 13, 2014, published as U.S. Patent Application Publication No. 2014/0248577 A1, which is a national phase entry under 35 U.S.C. § 371 of International Application No. PCT/US2012/039569 filed May 25, 2012, published as International Publication No. WO 2012/162605 A2, which claims the benefit of the filing date of U.S. Provisional Application No. 61/490,361, filed May 26, 2011, entitled Dental Tool and Guidance Devices, all of which are hereby incorporated herein by reference.

FIELD OF THE TECHNOLOGY

The present invention relates to devices and methods for preparing teeth for tooth restorations, and in particular it relates to systems, devices and methods for teeth to receive previously produced tooth restorations.

BACKGROUND OF THE INVENTION

Complete, intact teeth that are cosmetically desirable, that wear evenly and provide a balanced bite are the objectives of patients. Over time, however, problems arise in teeth due to accidents, deterioration from wear and tear, decay, tooth movement, etc. As a result, teeth may become accidentally chipped or cracked from a variety of causes including normal wear and tear, and weakened from decay due to the mouth hygiene and care practices and/or by consumption of certain foods such as sweets, use of tobacco, disease, medications, certain congenital conditions, and environmental effects. To this end, dental practitioners and their patients have relied on a variety of methods to repair these deformities and weaknesses of the teeth.

The repair of teeth often requires preparation and modification of the exterior shape and size of a tooth to be able to receive various prostheses or restorations such as crowns, inlays, onlays, bridges, and veneers. Also, to prepare the appropriate prosthesis or restoration, either impressions or 3-dimensional scanning must be conducted of the original unmodified tooth and the modified tooth. Dental practitioners often place a temporary prosthesis over the modified or prepared tooth while a permanent prosthesis is manufactured, but the use of such a temporary device and the removal of any cement used to place the temporary device over the prepared tooth may create a discrepancy between the prepared tooth and the internal configuration of the prosthesis.

A need has existed in the art to develop a system for more efficiently and reliably treating the teeth of patients for receiving restorations and other prosthesis.

BRIEF SUMMARY OF THE INVENTION

In accordance with the present invention, a system, methods and products have been discovered which provide a simpler, more reliable and more convenient technique for treating a tooth in need of a restoration part, in view of decay, cracks or other maladies existing in the tooth. There is provided a system of dental devices that may be used to modify a tooth by limiting the removal of tooth material to produce a shape or configuration that mates with or corresponds to the interior configuration of a restoration part. This system makes it possible to prepare a restoration part in advance of the preparation of the tooth. Also, the tooth can be accurately prepared with the configuration that corresponds to and mates with the internal configuration of the restoration part. By following this technique, the restoration part is available to be installed immediately after the preparation of the tooth. Therefore, in a single office visit, it is possible for the dentist to prepare the tooth and mount the restoration part onto the prepared tooth.

Under both of these conventional methods and the present invention, there is first a diagnosis indicating the need to treat a tooth with a restoration part. Normally, this is based on initial x-rays or other diagnostic techniques that identify the location and extent of decay, cracks or other maladies of the tooth. A mold, cast, impression, or three-dimensional data must be created based on the original tooth to be treated. At this point the present invention departs from conventional techniques in practice. Conventional techniques require the tooth to be revised and reshaped to remove decay, cracks and other maladies to leave a prepared tooth for receiving a restoration part. After tooth material has been removed, the revised configuration of the prepared tooth must be defined from a second mold or cast or three-dimensional data. The prepared, revised tooth is normally fitted with a temporary crown, to protect the prepared tooth and provide some comfort for the patient until the restoration part is manufactured, which can take days to weeks. Both sets of casts/molds or data are used, usually at an off-site laboratory, to prepare the restoration. The original tooth configuration is the basis for preparing the exterior of the restoration part while the prepared, revised tooth configuration is the reverse or negative for the configuration of the interior of the restoration part.

The procedure of the present invention reduces inconveniences to patients such as eliminating some office visits, and eliminating the need for wearing a temporary crown. Therefore, under the present invention there is no need to prepare the tooth prior to producing the restoration part. There is also no need to produce a cast, mold or three-dimensional data for the prepared tooth prior to installing the restoration part. There is no need for a temporary crown to be installed over the prepared tooth, nor the removal of the temporary crown and associated cement which can create complications with the fit of the restoration part. Such complications can require further revision of the tooth to fit the restoration or further modification of the restoration part. Also eliminated is the discomfort to the patient in wearing a temporary device and the greater risk of infection while the prepared tooth is exposed or is under the temporary crown.

In accordance with the present invention, a system of devices has been discovered for use in the treatment of a tooth to remove certain predetermined portions of the structure of the tooth. The system comprises:

(i) a dental instrument for removal of portions of a tooth in the mouth of a patient, said dental instrument adapted to be utilized with an overlay that is installed over or near the tooth to be treated; and (ii) an overlay for temporary installation into the mouth of a patient to guide a dental instrument in the removal of tooth structure of the treated tooth, said overlay including a cutting guide utilized with an appropriate dental instrument to limit the movement of the dental instrument during operation to restrict tooth structure removal to the predetermined portion of the tooth, said cutting guide comprising one or more of the following:

(a) one or more sets of guide walls, wherein the adjacent guide walls in each set and their surfaces have a predetermined configuration capable of contacting one or more guide projections of a dental instrument to limit the movement of the dental instrument and restrict tooth structure removal to the predetermined portion of the tooth; and (b) a receptacle hingedly or slidedly connected to the overlay and capable of receiving and attaching to the dental instrument, wherein the dental instrument when attached to the receptacle, has limited movement with respect to the tooth to be treated and which restricts tooth structure removal to the predetermined portion of the treated tooth.

With respect to the dental instrument, it comprises: a tooth treatment assembly for removing a portion of tooth structure; and one or more guide projections extending from the instrument in the direction of the working tooth to be treated when the instrument is in position for tooth structure removal, said one or more guide projections being capable of contacting a cutting guide in an overlay device installed in the vicinity of the tooth to be treated to limit the three-dimensional movement of the tooth treatment instrument with respect to the working tooth.

The dental overlay can include the cutting guide as described above or can include other embodiments of the cutting guide in which a receptacle is used for attaching the dental instrument to the overlay where the receptacle is hingedly or slidedly attached to the overlay. When the dental instrument is attached to such a receptacle of the overlay, because the movement of the receptacle is specially limited, the movement of the dental instrument is also limited which restricts its ability to remove tooth structure from the treated tooth to the predetermined portion of the treated tooth.

In another embodiment of the invention a method is provided for treating a working tooth in a patient's mouth by removing portions of its structure, said method comprising the steps of:
  determining the three-dimensional structure of the working tooth to be removed for treatment;
  providing the dental instrument comprising a tooth cutting element for removal of a portion of a tooth's structure and one or more guide projections extending from the instrument in the direction of the tooth to be treated when said tooth treatment element is in operating position for tooth structure removal;
  preparing a dental overlay having a cutting guide with a configuration that is capable of contacting one or more guide projections of the dental instrument to limit the movement of the dental instrument to restrict the structure removed from the tooth under treatment to the predetermined three-dimensional portions of tooth structure for the treatment.

These and other embodiments and further details of the invention are elsewhere described in the specification.

BRIEF DESCRIPTION OF THE DRAWINGS

The invention will now be described in more detail with respect to non-limiting drawings illustrating some preferred embodiments of the invention. In the drawings.

Within the drawings, the same or similar reference numeral is used to correspond to the same or an analogous element.

DETAILED DESCRIPTION

Figure 1:
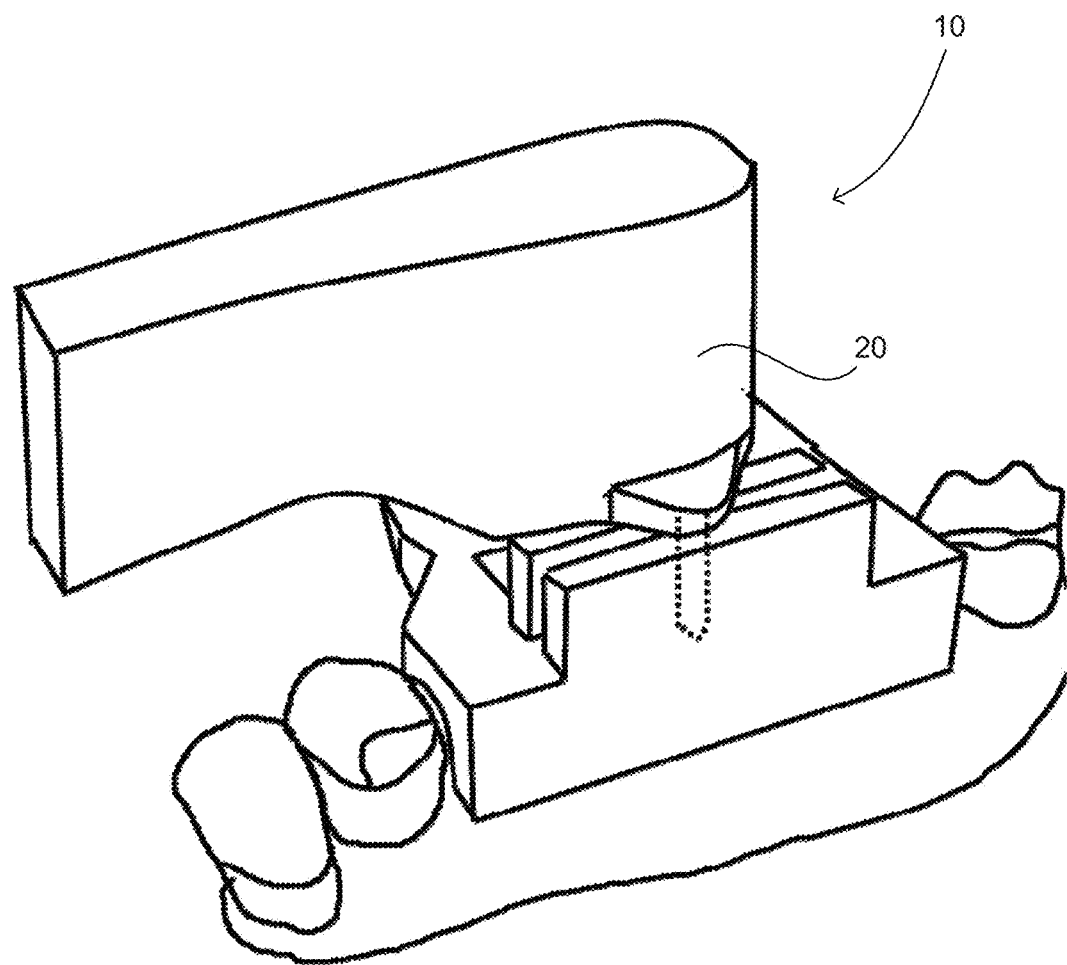
FIG. 1 is a perspective view showing a dental instrument placed in an overlay for use by a dentist in removing tooth structure in accordance with the present invention.

In the Brief Summary of the Invention above and in the Detailed Description of the invention herein, and the claims below, and in the accompanying drawings, reference is made to particular features (e.g., method steps) of the invention. It is understood that the invention embraces and includes all possible combinations of the features described in the text, in addition to those depicted in the drawings. For example, where a particular feature is disclosed in the context of a particular aspect, arrangement, or embodiment of the invention, or a particular claim, that feature can also be used, to the extent possible, in combination with and/or in the context of other particular aspects, arrangements, and embodiments of the invention, and in the invention generally.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can consist not only of components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility). The term "step of" does not mean "step for".

The terms "lower," "upper," etc. and derived directional terms such as "horizontal", "vertical", "upward", and "downward" are based on a normal configuration of an overlay as shown in the drawings, wherein the overlay fits onto the lower teeth of a patient with their roots extending vertically downward. The term dentist in this text is not be interpreted restrictively and can also be read as dental practitioner, dental technician, dental assistant, dental auxiliary, dental therapist, dental designer, etc.

The present invention provides for a system for use by a dental practitioner ("dentist") in precisely preparing, revising, or modifying a working tooth for receipt of a preformed restoration such as an inlay, onlay, crown, bridge, or veneer. Such a system has two main components: (i) a dental instrument having features capable of contacting a suitable guiding configuration of an overlay or overlay device and (ii) an overlay or overlay device which can be attached to a working tooth and/or neighboring teeth and configured to limit the three-dimensional movement of a dental instrument, thereby limiting the movement of the dental instrument itself with respect to the tooth being treated. A method of use of the system is further provided in accordance with the present invention.

According to conventional techniques, a diagnostic evaluation of a tooth reveals an existing condition requiring the tooth to be treated by installation of a restoration or prosthesis. Under these conventional approaches, the tooth to be treated is revised and prepared first, and then its revised configuration is used to fabricate the internal configuration of the restoration. Therefore the restoration is fabricated to fit the already prepared tooth.

According to the invention, the system comprising the overlay with a cutting guide and the dental instrument which coordinates with the overlay enables the tooth to be prepared after fabrication of the restoration, where the prepared tooth conforms to the configuration of the existing restoration.

The dentist can prepare a cast or mold of the existing working tooth in the context of neighboring teeth and can identify by x-ray and/or other diagnostic techniques the portions of the working tooth that should be removed, due to e.g., decay, cracks, weaknesses, deterioration, impediment to bite, etc. Based on this information, the invention provides for producing a restoration part, in advance of the physical revision of the tooth so that this restoration part is available to the dentist even before he or she starts physically preparing the tooth. The tooth can then be prepared with precision by using the configured overlay to revise the tooth in a manner to correspond to or mate with the interior of the restoration. The availability of the restoration makes it possible to mount it directly onto the tooth in the same visit that the tooth is prepared. This substantially reduces inconvenience of the patient and reduces the number of visits made to the dentist. This also reduces the possibility of a prepared tooth becoming contaminated during the extended time period between tooth preparation and installation of the final restoration.

Referring now to the drawings, FIG. 1 shows a preferred embodiment of a dental instrument 10 adapted to fit and to coordinate with an overlay device for use in removing portions of tooth structure pursuant to a predetermined configuration, to prepare a working tooth to receive a preformed restoration. In this embodiment, the dental instrument 10 has a hand grip 30 attached to a tooth treatment assembly 50, including for example a dental bur, that is installed within and encapsulated by a projection head 20. As shown in FIG. 1, the tooth treatment assembly and the projection head may be integrated with one another so as to form a monolithic structure described further herein.

Figure 2:
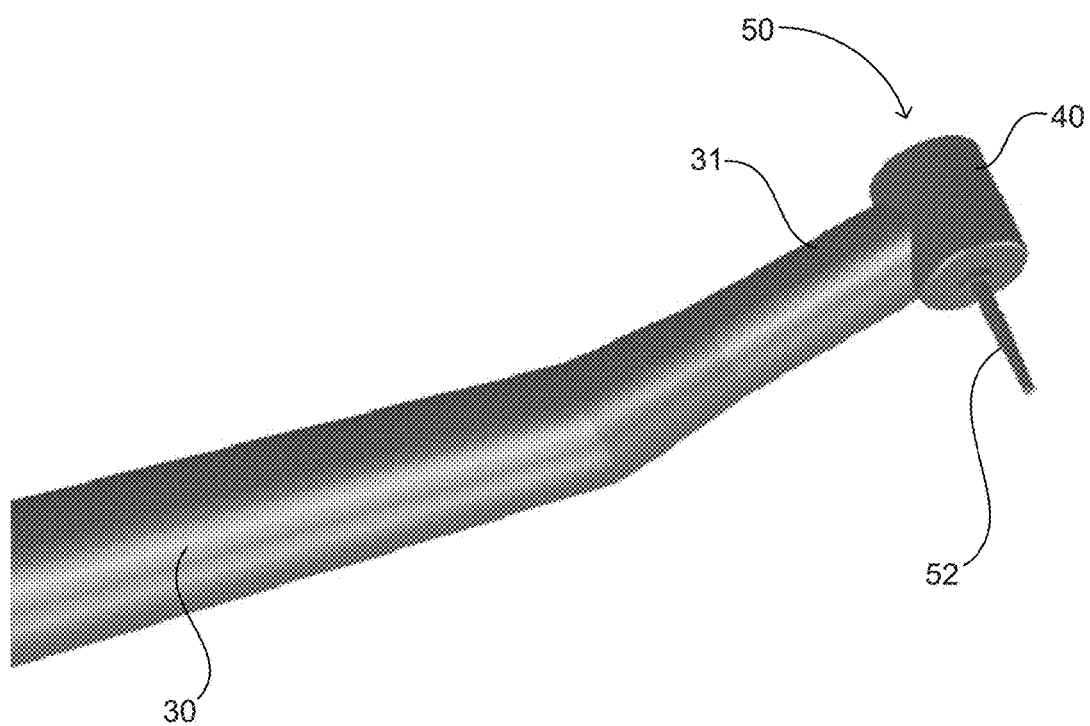
FIG. 2 is a perspective view showing a hand grip and a tooth treatment assembly of the dental instrument of FIG. 1.
Figure 15:
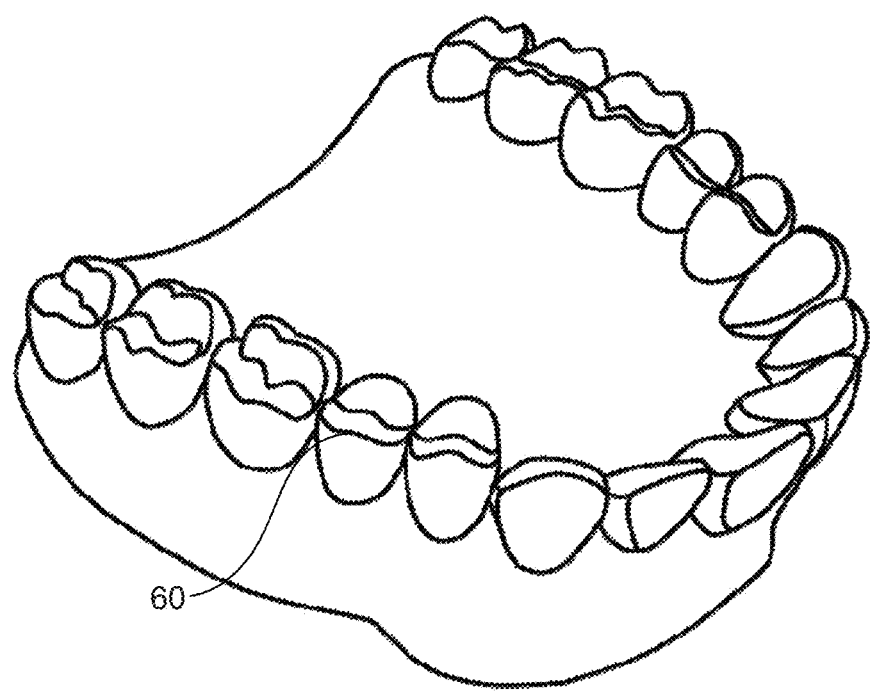
FIG. 15 is a perspective view of a tooth prior to any preparation of the tooth.

As illustrated in FIG. 2, the hand grip 30 provides a portion of the instrument 10 for resting in a human hand and has a shaft that optionally may be hollow along its longitudinal axis. One end of the hand grip 30 is attached to one side of a connecting end 31 which is attached on its other side to the tooth treatment assembly 50. The tooth treatment assembly 50 of FIG. 2 is used when the tooth treatment assembly 50 does not form an integrated, monolithic structure with the projection head 20. The tooth treatment assembly 50 includes a tooth treatment element 52, and appropriate pneumatic and/or mechanical drives well-known in the art that run through the hand grip 30 and may include a housing 40. However, the housing 40 forms part of the projection head 20 in the arrangement in which the tooth treatment assembly 50 and projection head 20 are integrated. In this preferred embodiment, the mechanical drives cause a rotation of a tooth treatment element 52 used for removing tooth structure. It is important to note that the tooth treatment element 52 need not be rotated to accomplish its intended function of removing tooth structure from a working tooth 60, an example of which is shown in FIG. 15. For instance, it may cut through a working tooth in a sawing or milling action. The instrument can also be adapted for a tooth treatment element that removes tooth material by laser or other techniques.

Figure 3A:
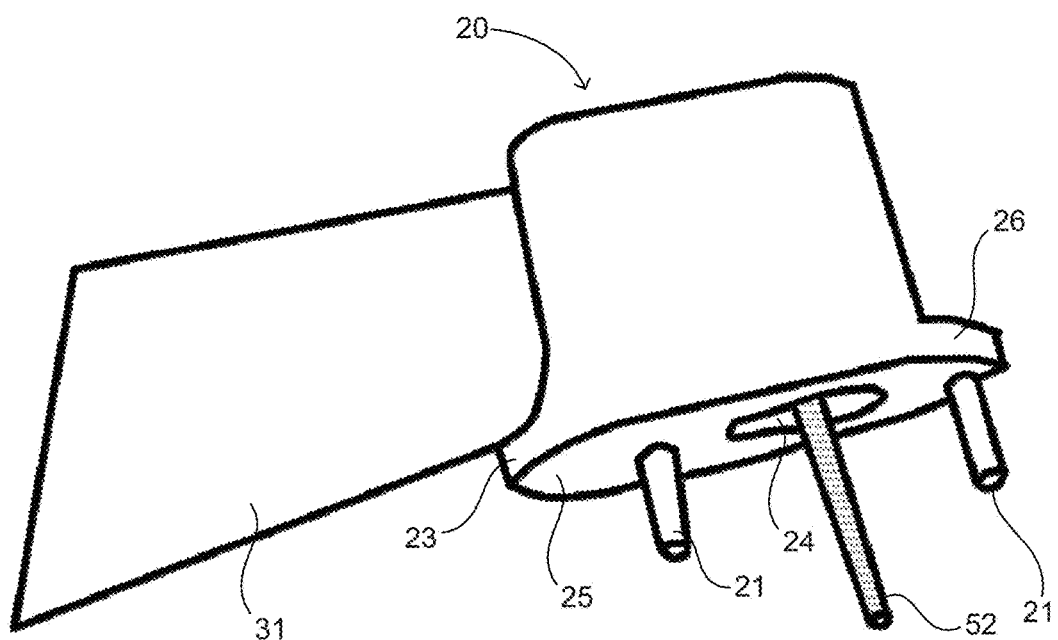
FIGS. 3A and 3B are perspective views of two configurations the tooth treatment assembly and a projection head of the dental instrument shown in FIG. 1.
Figure 3B:
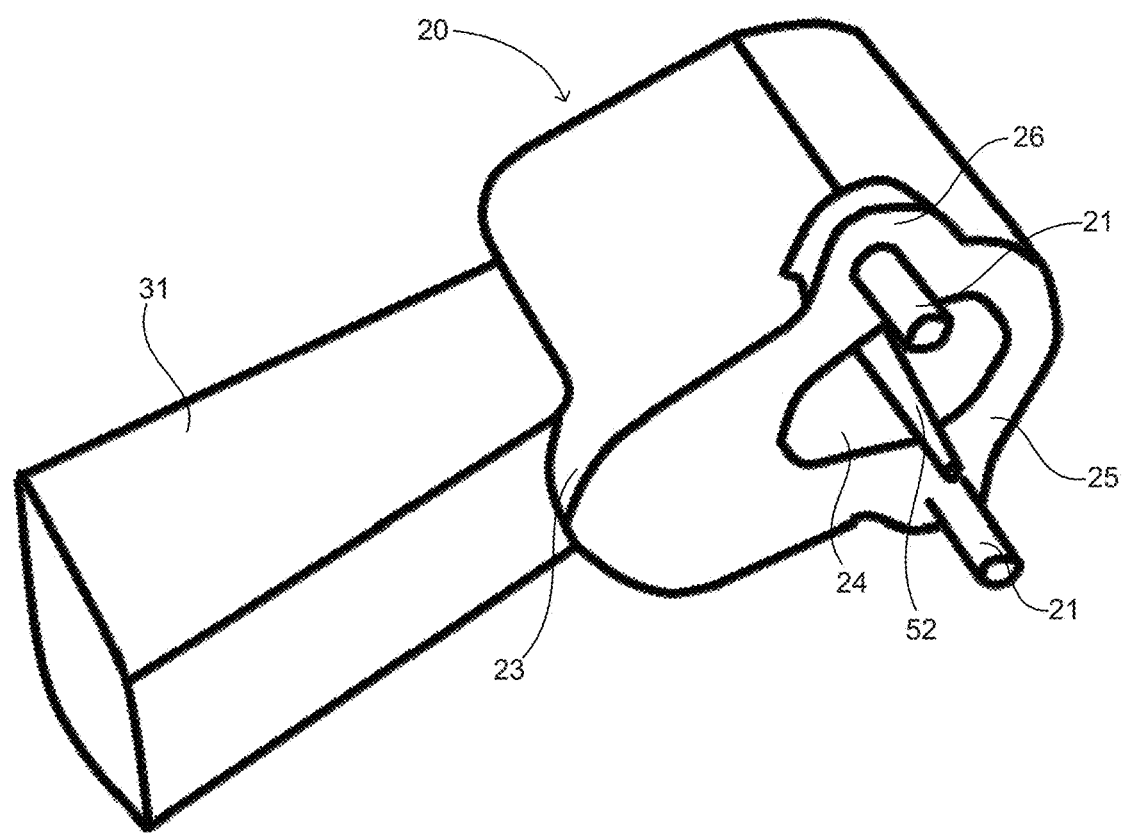
Figure 4A:
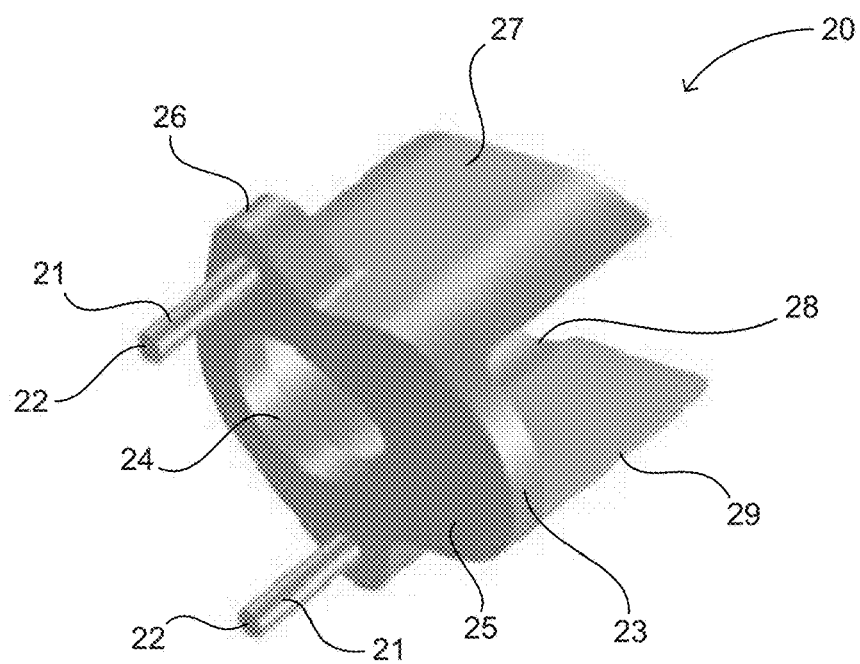
FIGS. 4A and 4B are plan views of two configurations of the projection head and the tooth treatment assembly shown in FIGS. 2 and 3.
Figure 4B:
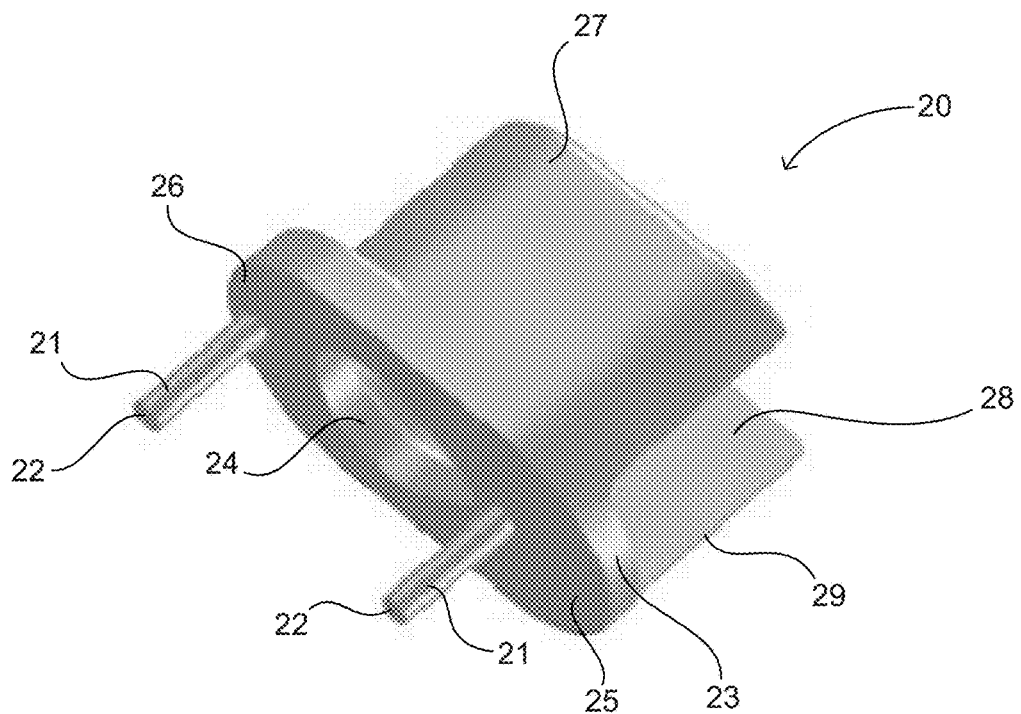

As shown in FIGS. 2-4, the projection head 20 surrounding the tooth treatment assembly 50 preferably has a bottom base 23 from which a side wall 27 extends upwardly and around the periphery thereof leaving an opening 29 on one end. The opening 29 is large enough to accommodate the thickness of the connecting end 31 of the hand grip 30. In the two-piece arrangement of the tooth treatment assembly 50 and the projection head 20, an interior face 28 of the side wall 27 of the projection head 20 preferably wraps around the periphery of the bottom base 23 such that a portion of the side wall 27 approximately conforms to the shape of the housing 40 of the tooth treatment assembly 50. In either arrangement, a tool aperture 24 extends through the thickness of the bottom base 23 and has a shape and size to enable it to accommodate the tooth treatment assembly 50 and to allow water jets or air streams from the tooth treatment 50 assembly to pass through to the working tooth 60. In the preferred embodiment, guide projections 21 extend downwardly from a projection flange 26 that protrudes, often in a horizontal direction away from the bottom base 23 as shown in FIGS. 1 and 3, from the bottom base 23. Alternatively, one or more of these projections 21 could also extend from the bottom base 23 itself. In another alternative arrangement, the projection flange 26 could protrude from a combination of the bottom base 23 as well as the side wall 27.

The guide projections 21 are capable of contacting physical limits, such as those defined by guide surfaces, of a suitable guiding configuration of a predetermined overlay device. In this manner, the suitable guiding configuration can limit the lateral movement of the tooth treatment assembly 50 and corresponding tooth treatment element 52 with respect to the tooth being prepared.

The guiding configuration provides a corresponding limitation on the movement of the entire dental instrument 10 by the user and thus can remove predetermined portions of tooth structure such that when movement of the dental instrument 10 throughout the guiding configuration is complete, the resulting prepared tooth 70, an example of which is shown in FIG. 15, will have dimensions that enable it to be fitted to and mated with the interior of a preformed restoration.

In one embodiment, the projection head 20 is capable of resting on a suitable guiding configuration. Within this configuration, the bottom base 23 of the projection head 20 preferably may have a flat bottom surface 25 as shown in FIG. 3 or a curved surface (not shown), but other arrangements of this surface are within the scope of the present invention. The guide projections 21 extending from the projection head 20 in this configuration preferably have a predetermined length to correspond with the guiding configuration of the overlay device. In this manner, the guide projections 21 will preferably have a length such that each of their ends or extremities 22 do not contact a surface of the suitable guiding configuration when the projection head 20 rests upon a suitable guiding configuration. Because the projection head 20 rests upon the suitable guiding configuration in this arrangement, the guiding configuration limits the movement of the projection head 20 towards the guiding configuration and thus controls the depth of the projection head 20 and thus the tooth treatment assembly 50 and ultimately the depth of penetration of the tooth treatment element 52 into a working tooth 60.

Alternatively, the guide projections 21 may have a predetermined length such that each of their ends 22 does contact a surface of the suitable guiding configuration. In this manner, the guiding configuration limits the movement of the guide projections 21 towards the guiding configuration and accordingly controls the depth of the projection head 20 and ultimately the depth of penetration of the tooth treatment element 52 into a working tooth. In such an arrangement, the projection head 20 may but need not rest upon the guiding configuration.

In some cases, a suitable guiding configuration used in conjunction with the preferred embodiment of the dental instrument 10 may have various spacings amongst its elements. The projection head 20 may be selected with a size and shape that enable it to fit within only preselected or certain of these spacings. For instance, a set of adjacent guide surfaces extending from the base of a suitable guiding configuration may have stepped, or a series of, spacings between guide surfaces, whereby only some of the adjacent guide surfaces will be sufficiently spaced to enable the projection head 20 of the dental instrument to fit.

Figure 5:
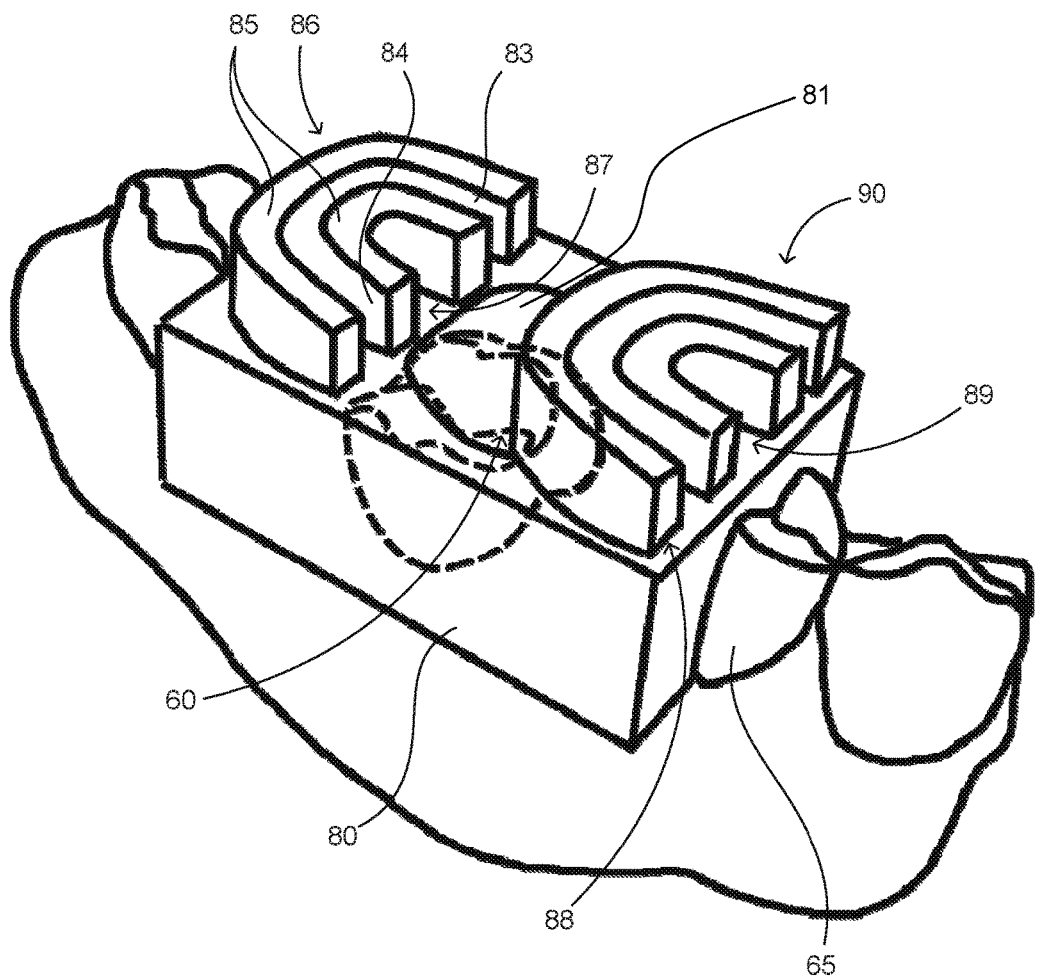
FIG. 5 is a perspective view of a dental overlay placed on a patient's teeth for use by a dentist in removing tooth structure in accordance with the present invention.
Figure 6:
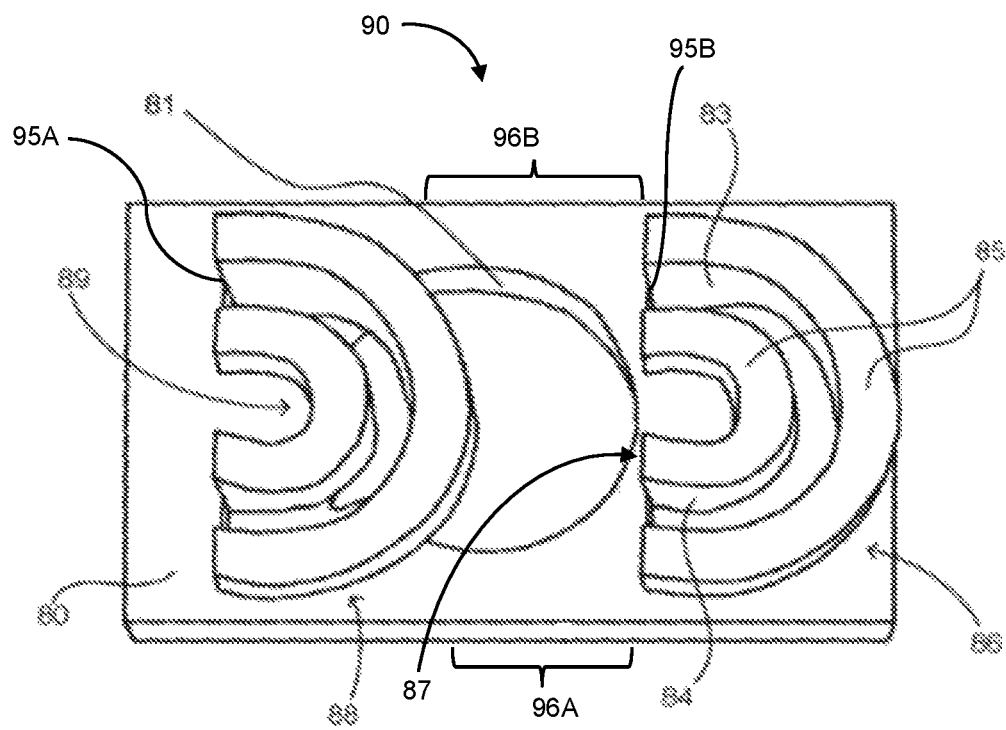
FIG. 6 is a plan view of the dental overlay shown in FIG. 5.
Figure 7:
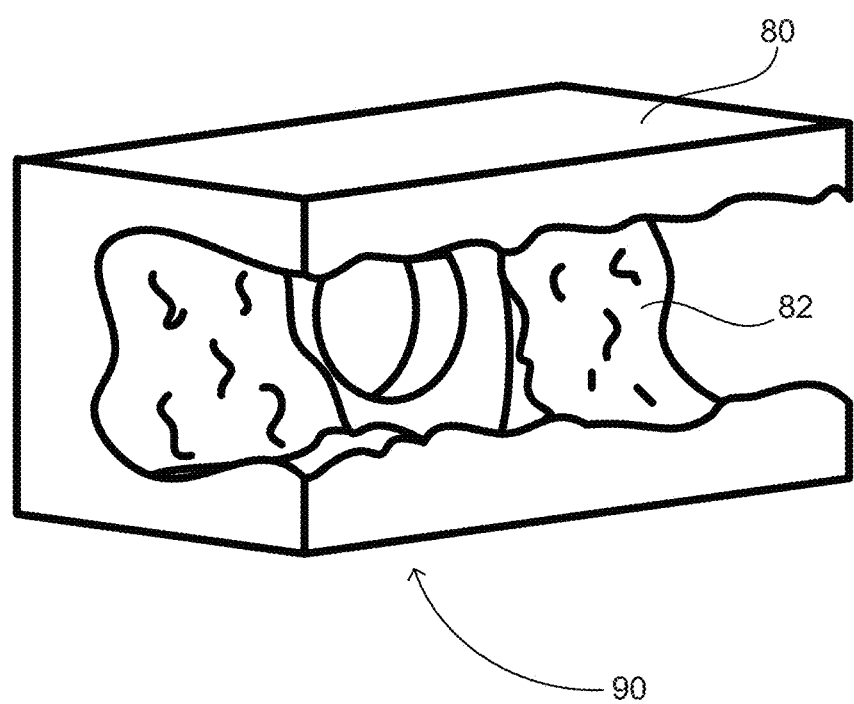
FIG. 7 is a bottom view of the dental overlay shown in FIG. 5.

In another embodiment of the invention, an overlay may be adapted to receive or accommodate a dental instrument, such as the dental instrument 10 previously described herein. FIGS. 5-12 show preferred configurations of such an overlay. In the preferred configurations shown in FIGS. 5-7, an overlay 90 has a predetermined base 80. This base 80 has an open area 81 that extends through the thickness of the base 80 and exposes surfaces of the working tooth 60 or adjacent teeth 65 at least larger than the portions of the tooth structure to be removed. Furthermore, as illustrated in FIG. 7, the base 80 has tooth contacting surfaces 82 that are contoured to provide contact regions capable of contacting one or more teeth to secure the overlay 90 in a suitable position for the predetermined overlay configuration to be used in removing the predetermined portions of tooth structure from the tooth 60 being treated. In this regard, the tooth contacting surfaces 82 may have a shape that substantially corresponds to the outer shape of portions of the working tooth and/or teeth adjacent to the working tooth.

In this arrangement, a first guide wall 86 and a second guide wall 87 which form a first set of guide walls extend vertically from one side of the base 80. As shown in FIGS. 5 and 6, third and fourth guide walls 88, 89 forming a second set of guide walls similarly extend vertically from an opposite side of the base 80. Although not shown in the figures, an overlay may have additional sets of guide walls. Each set of guide walls in the preferred embodiment shown in FIGS. 5 and 6 has first and second guide surfaces 83, 84 on guide walls 86, 87, respectively. However, a set of guide walls may have more or less than two guide walls.

Figure 8:
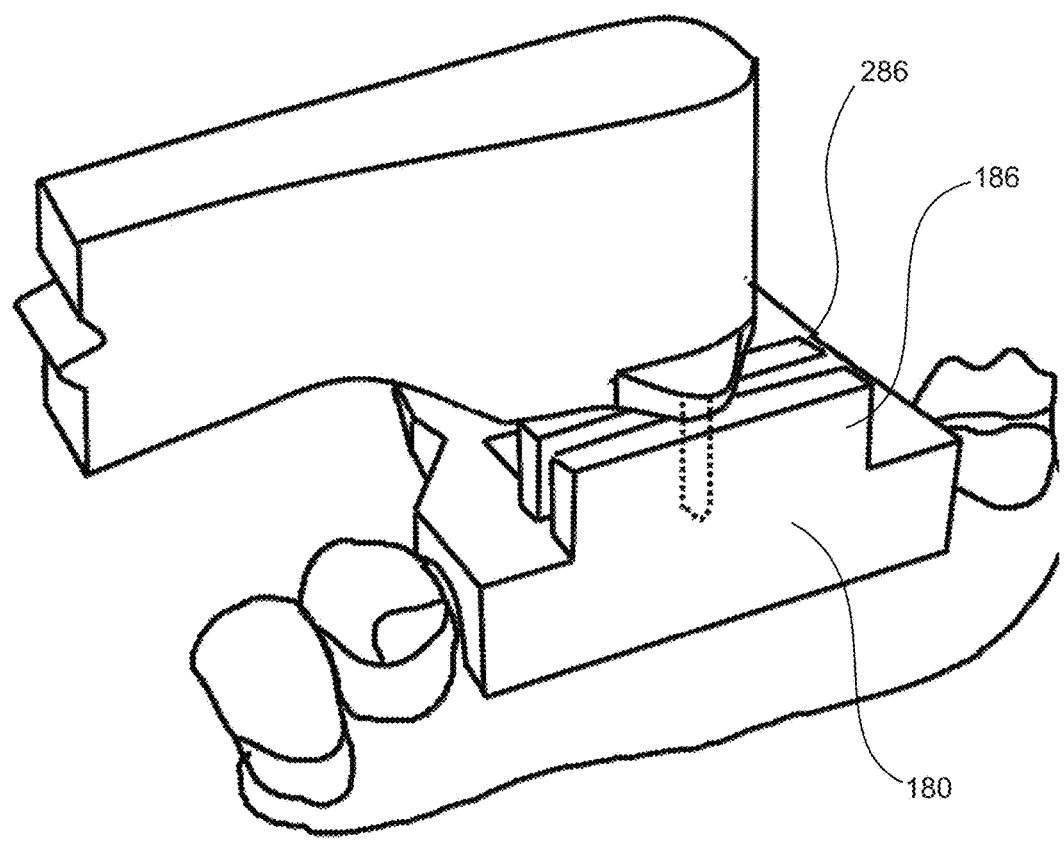
FIG. 8 is a perspective view of an alternative arrangement of an overlay placed on a patient's teeth for use by a dentist in removing tooth structure in accordance with the present invention.
Figure 9:
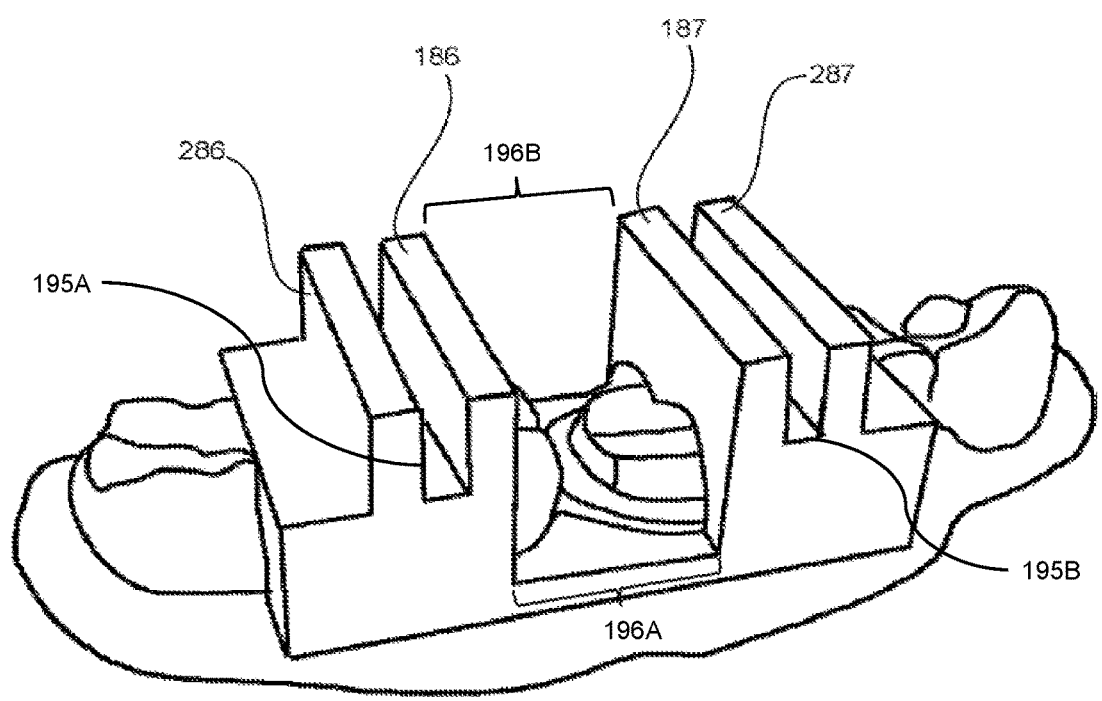
FIG. 9 is a perspective view of a further alternative arrangement of an overlay placed on a patient's teeth for use by a dentist in removing tooth structure in accordance with the present invention.

In the preferred embodiment shown in FIGS. 5 and 6, the first and second guide walls 86, 87 are positioned distally along the base 80 whereas the third and fourth guide walls 88, 89 are positioned mesially along the base 80. However, a set of guide walls may be positioned on the buccal or facial and/or lingual or palatal sides of a comparable base 180, as illustrated in FIG. 8. In the preferred embodiment, the first and second guide surfaces 83, 84 of respective guide walls 86, 87 are capable of contacting one or more guide projections of a dental instrument to limit the movement of a tooth treatment element of a dental instrument, such as tooth treatment element 52 of dental instrument 10. Preferably, guide surfaces 83, 84 of each of respective guide walls 86, 87, in combination with base 80, define respective side apertures 95A, 95B and are spaced apart a sufficient distance to each receive such a guide projection. As further shown, guide wall 86 of each set of guide walls 86, 87, in combination with base 80, define opposing side openings 96A, 96B and are spaced apart a sufficient distance to receive a tooth treatment element of a dental instrument, such as tooth treatment element 52 of dental instrument 10.

In the preferred embodiment shown in FIGS. 5 and 6, the guide walls 86, 87 have a substantially uniform thickness in a direction perpendicular to the base 80 lending to a substantially flat surface across the top surface 85 of each of the guide walls 86, 87. Furthermore, guide walls 86, 87 have a substantially equivalent predetermined height above the base 80 which, when coupled with the substantially flat top surface 85, permits a portion of a dental instrument, such as the projection head 20 of the dental instrument 10, to lay across the thickness of adjacent guide walls, often laying flat as in the arrangement shown in FIG. 1. In this manner, the predetermined height of guide walls 86, 87 can limit the movement of a tooth treatment element, such as the tooth treatment element 52 of dental instrument 10, in the direction, which is often the apical direction, of the tooth. In an alternative arrangement, the top surface of a set of guide walls may have a bevel, chamfer, round, indent, or have an alternative shape to allow an overlay to receive a surface of a dental instrument at a variety of angles.

Preferably, during the tooth preparation procedure the overlay 90 should remain fixed and not move once it is placed around the working tooth 60. Moreover, the overlay 90 should remain in a stable position even when a dental instrument intended for use with the overlay 90, such as dental instrument 10, makes contact with it. The position of the overlay 90 can be secured by contact of the contacting surfaces 82 of the overlay 90 with tooth surfaces or by the use of a bonding agent, such as one that is light cured or a temporary cement or by projections from the overlay 90 that engage portions of a tooth, including the working tooth 60, either of the adjacent teeth 65, or dentition on the opposing jaw.

As in the preferred embodiments shown in FIGS. 5 and 6, the guide walls may be curved. In this arrangement, each guide wall within a set of guide walls is substantially curved about the same axis.

Figure 10:
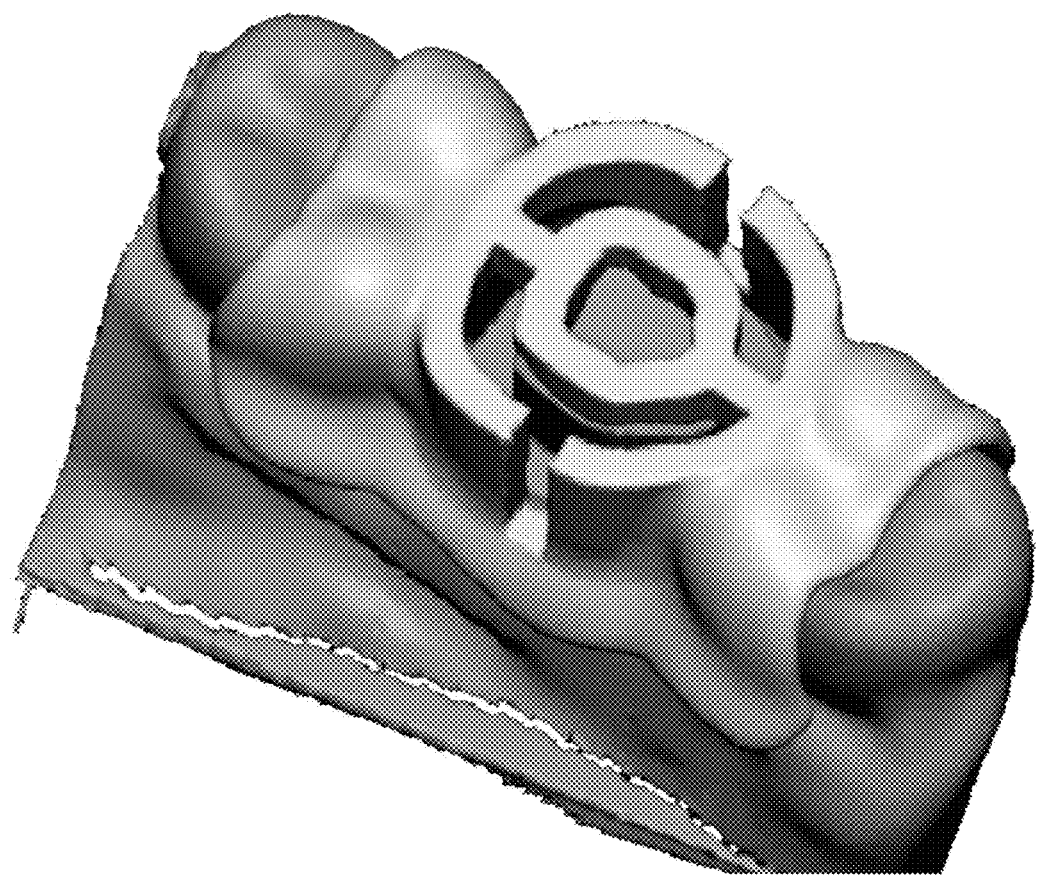
FIG. 10 is a perspective view of a still further alternative arrangement of an overlay placed on a patient's teeth for use by a dentist in removing tooth structure in accordance with the present invention.

In alternative arrangements of preferred embodiments, first and second guide walls of a given set of guide walls may be substantially parallel to one another in a direction parallel to a plane through the longitudinal center lines through the guide walls. For instance, in FIGS. 8 and 9, there are provided first and second guide walls 186, 187 and 286, 287 configured in a manner to limit the movement of a tooth treatment element of a dental instrument in directions substantially parallel to and substantially perpendicular to the proximal surfaces of each working tooth, respectively. Each set of guide walls 186, 286 and 187, 287 is capable of contacting one or more guide projections of a dental instrument to limit the movement of a tooth treatment element of a dental instrument, such as tooth treatment element 52 of dental instrument 10. Each set of guide walls 186, 286 and 187, 287, in combination with base 80A, define respective side apertures 195A, 195B to receive such a guide projection. As further shown, guide wall 186 and guide wall 187, in combination with base 80A, define opposing side openings 196A, 196B each having a side opening width measured in a first plane perpendicular to each set of guide walls 186, 286 and 187, 287 sufficient to receive a tooth treatment element of a dental instrument, such as tooth treatment element 52 of dental instrument 10. As shown, the side opening width is larger than a side aperture width of each of side apertures 195A, 195B measured in the first plane. In a further alternative arrangement, each guide wall within a given set of guide walls is nonparallel to each other guide wall. In such an arrangement, the spaces between the guide walls of a given set of guide walls may be arranged in a circular pattern as shown in FIG. 10. Although not shown in the figures, the guide walls may also be in a rectangular, triangular, or a number of other configurations.

Figure 11:
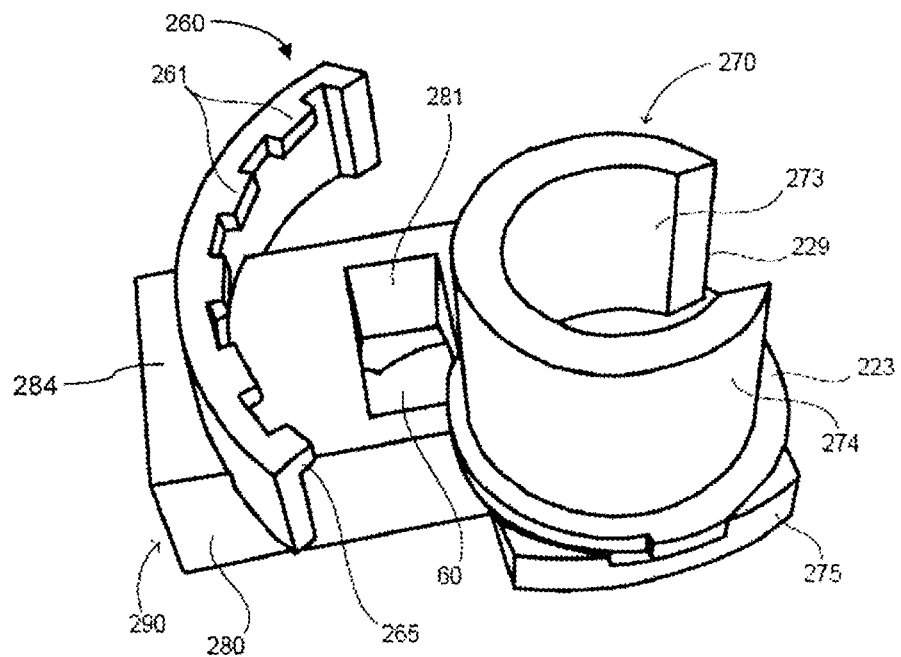
FIG. 11 is a perspective view of an overlay device for use by a dentist in removing tooth structure in accordance with the present invention.
Figure 12:
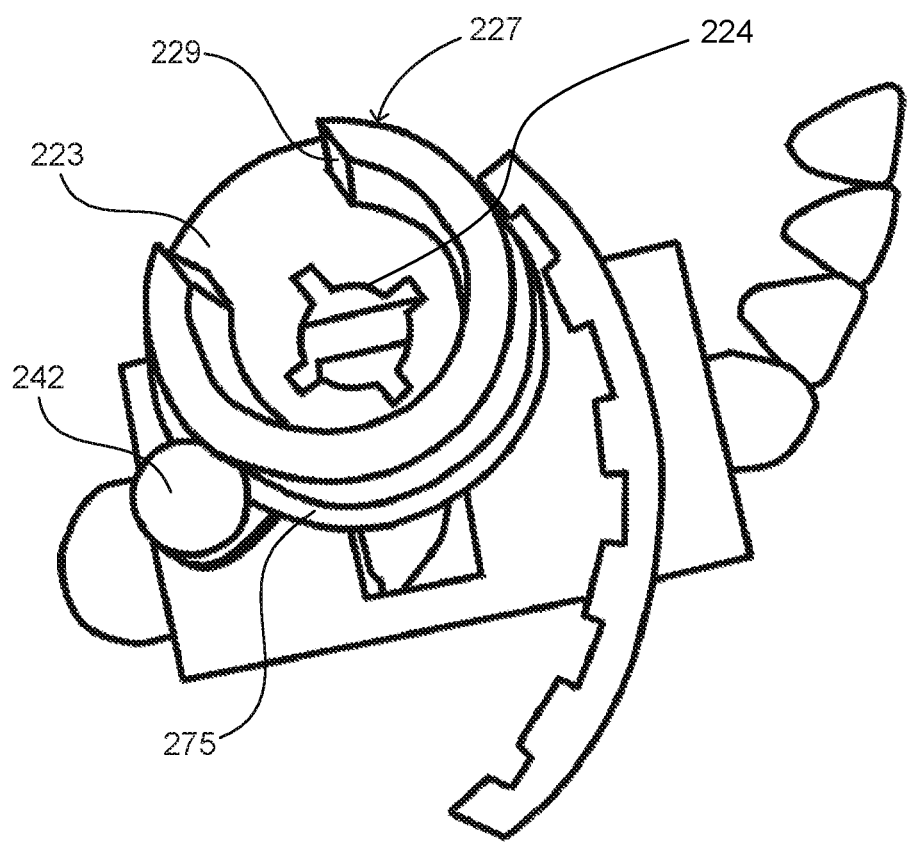
FIG. 12 is a plan view of the overlay device shown in FIG. 11 placed on a patient's teeth for use by a dentist in removing tooth structure.
Figure 13:
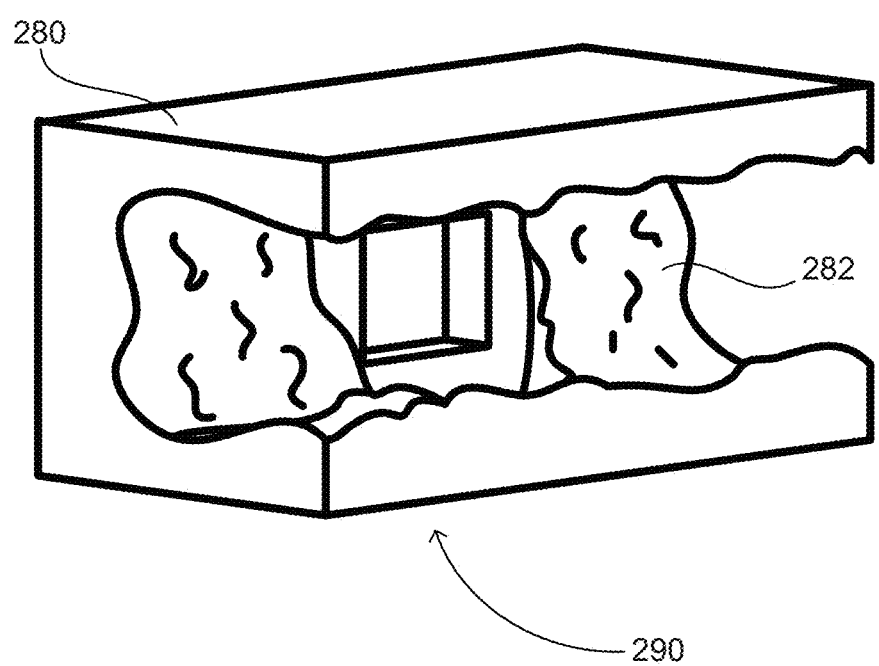
FIG. 13 is a bottom view of the overlay device shown in FIG. 11.

FIGS. 11-13 illustrate another preferred embodiment for a dental instrument for use in removing a portion of the structure of a working tooth 60 in preparation for a subsequent restoration. The dental instrument includes a hand grip attached to a tooth treatment assembly, often through a connecting end. The tooth treatment assembly preferably includes a housing, a tooth treatment element, and appropriate pneumatic and/or mechanical drives as in the tooth treatment assembly 50.

The housing of the tooth treatment assembly is adapted to connect to, and preferably to fit within, a receptacle element portion of an overlay device, such as a receptacle 270 of an overlay 290 described further herein, and is further capable of interlocking with the receptacle. In an alternative arrangement, the housing of the tooth treatment assembly may have certain features for increased stability of the dental instrument. Such features may include a non-circular or asymmetric cross-section or interlocking grooves on the exterior capable of interfacing with an overlay device.

With reference to FIG. 11, the tooth treatment assembly of the dental instrument may be fixed to a receptacle element of the overlay such that it is capable of moving in tandem with the receptacle. In one such arrangement, the tooth treatment assembly may be integrally connected to a receptacle, such as the receptacle 270, such that it is capable of pivoting about a hinge, such as a hinge 242, that connects the receptacle to an overlay device, such as the overlay 290.

Again referring to FIG. 11, when the tooth treatment assembly is attached to a receptacle element connected to an overlay device, the tooth treatment element may protrude through the receptacle element and may extend into an open area of the overlay device, such as the open area 281, such that it is capable of contacting physical limits of a suitable guiding configuration provided by open area 281, of a predetermined overlay device to provide the tooth treatment element with sufficient access to a three-dimensional portion of the tooth to be removed. In this manner, the suitable guiding configuration may act in coordination with the receptacle element to limit the lateral movement of the tooth treatment assembly and corresponding tooth treatment element with respect to the tooth 60 being prepared.

Figure 16:
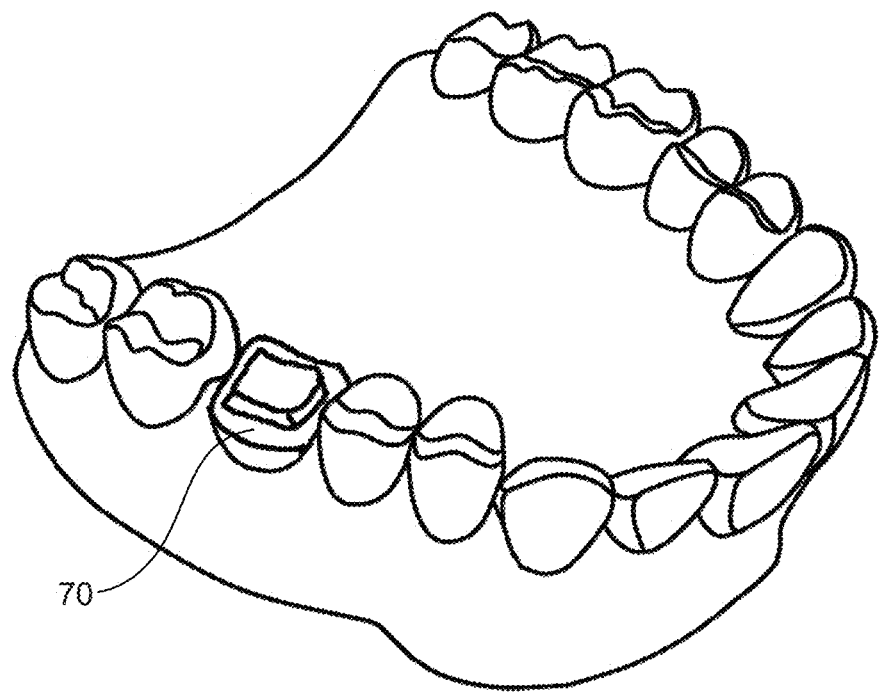
FIG. 16 is a perspective view of the tooth shown in FIG. 15 after preparation of the tooth using the dental instrument of FIG. 1 in combination with the dental overlay of FIG. 5 in accordance with the present invention.

The guiding configuration and receptacle element thus provide a corresponding limitation on the movement of the entire dental instrument by the user and thus the instrument can remove predetermined portions of tooth structure such that when movement of the dental instrument throughout the area through which the receptacle element permits movement within the guiding projection, the resulting prepared tooth 70, an example of which is shown in FIG. 16, will have dimensions that enable it to be fitted to and mated with the interior of a preformed restoration.

In the arrangement shown in FIG. 11 in which the tooth treatment assembly is installed within a receptacle element attached to an overlay, such as the receptacle 270, the overlay may restrain the vertical movement of the receptacle element to limit the movement of the tooth treatment assembly towards the guiding configuration and thus ultimately control the depth of penetration of the tooth treatment element into the working tooth 60.

In another embodiment in accordance with the invention, an overlay 290 may be adapted to receive or accommodate a dental instrument, such as the dental instrument previously described herein. The overlay 290 has a predetermined base 280 that has an open area 281 that extends through the thickness of the base 280 and exposes surfaces of the working tooth 60 or adjacent teeth 65 at least larger than the portions of the tooth structure to be removed as well as a receptacle 270 attached to the base 280. Furthermore, as illustrated in FIG. 13, the base 280 has tooth contacting surfaces 282 that are contoured to provide contact regions capable of contacting one or more teeth to secure the overlay 290 in a suitable position for the predetermined overlay configuration to be used in removing the predetermined portions of tooth structure from the tooth 60 being treated. In this regard, the tooth contacting surfaces 282 may have a shape that substantially corresponds to the outer shape of portions of the working tooth and/or teeth adjacent to the working tooth.

As shown in FIGS. 11 and 12, the receptacle 270 is a feature that is adapted to receive and may congruously surround a portion of a housing of a tooth treatment assembly, such as the housing 240 of the tooth treatment assembly, when the housing is installed within the receptacle 270. The receptacle 270 preferably has a bottom base 223 from which a side wall 227 extends upwardly and around the periphery thereof leaving an opening 229 on one end. The opening 229 is large enough to accommodate the thickness of the connecting end of the hand grip. A combination of the bottom base 223 and the side wall 227 form inner and outer surfaces 273, 274 of the receptacle. The inner surface 273 of the receptacle 270 preferably conforms to the shape of a housing of the tooth treatment assembly, such as the housing of the tooth treatment assembly. The receptacle 270 may further have a head locking feature that is capable of engaging an undercut located on a housing of a tooth treatment assembly, such as the housing of the tooth treatment assembly, and a shaft locking feature that is capable of engaging an undercut located on a connecting end of a tooth treatment assembly, such as the connecting end of the tooth treatment assembly. The outer surface 274 of the receptacle 270 preferably includes a flange 275 extending therefrom. In a preferred arrangement in which the receptacle 270 is circular to conform to a similarly circular tooth treatment assembly, the flange 275 preferably extends circumferentially around the outer surface 274 of the receptacle 270, as in the arrangement shown in FIGS. 11 and 12. A tool aperture 224 extends through the thickness of the bottom base 223 of the receptacle 270 to enable a tooth treatment element as well as water jets or air streams to pass through.

Again referring to FIG. 11, the receptacle 270 may be movably attached to a base surface 284 of the overlay 290. In this manner, the receptacle 270 may be pivotally attached to the overlay 290 through the hinge 242 as shown in FIG. 11. In this manner, the receptacle 270 is capable of rotating about the longitudinal axis of the hinge. Although the hinge 242 is shown as a pin in FIG. 11, any type of a rotational connection between the overlay and the receptacle, such as attaching the receptacle to a roller bearing on the overlay, is within the scope of this invention.

As FIG. 11 further illustrates, when a dental instrument is attached to the overlay 290, a tooth treatment element of the tooth treatment assembly of the instrument may protrude through the tool aperture 224 and may extend into an open area 281 of the overlay 290 such that it is capable of contacting physical limits of a suitable guiding configuration defined by open area 281 of the overlay 290. The receptacle 270 may also include at least one guide projection (not shown) extending towards the open area 281. In this manner the base 280 is capable of coordinating with the hinge 242 and the open area 281 is capable of contacting either or both of the tooth treatment element or the guide projection to confine the movement of the receptacle 270 and thus the tooth treatment assembly to a predetermined three-dimensional region of the working tooth 60.

In an alternative arrangement, a receiving wall 260 is attached to the base surface 284 of the overlay 290. The receiving wall 260 has a rim 265 along its length. In a preferred arrangement, the receiving wall 260 may have notches 261, but alternative arrangements may not have these notches. The receiving wall 260 is preferably placed at a distance away from the hinge 242 such that, during rotation of the receptacle 270, the flange extending from the outer surface 274 of the receptacle 270 is capable of being received within a region between the base surface 284 and the rim 265 of the receiving wall 260. In this manner, the rim 265 may urge the receptacle 270 towards the base surface 284 as the receptacle 270 is rotated about the hinge.

Figure 14:
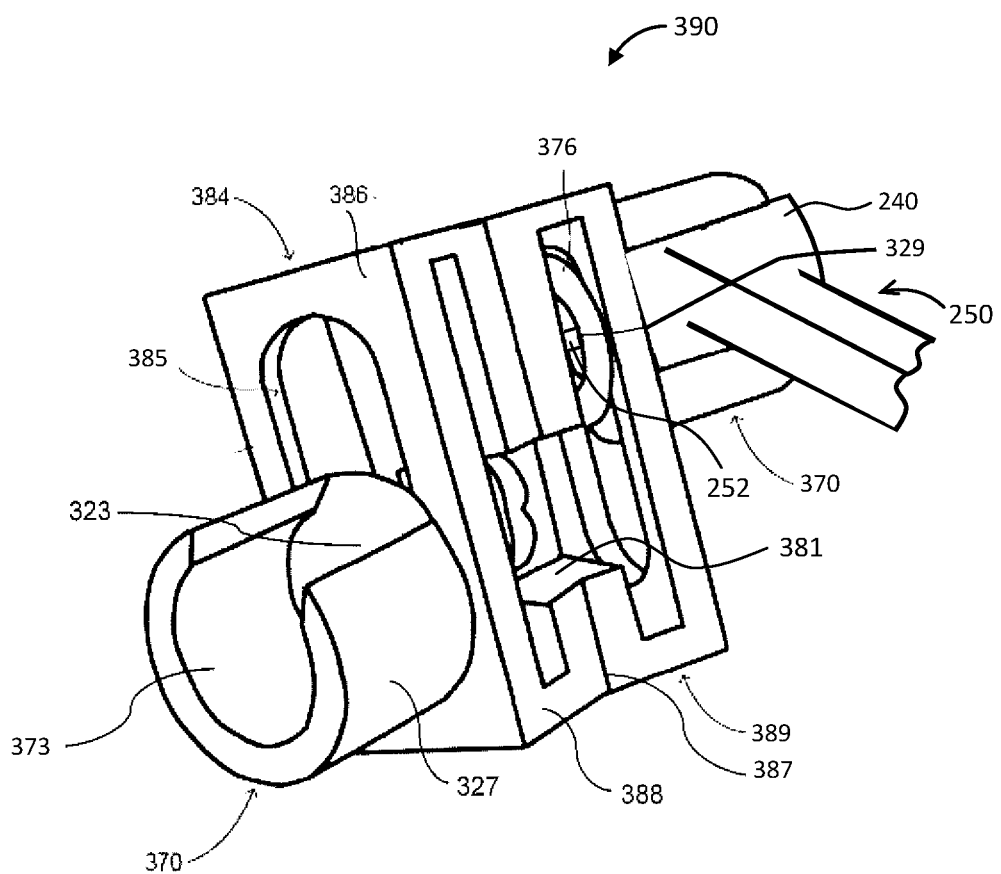
FIG. 14 is a perspective view of an overlay device placed on a patient's teeth for use by a dentist in removing tooth structure in accordance with the present invention.

In another alternative arrangement of this embodiment, as illustrated in FIG. 14, an overlay 390 may have tooth contacting surfaces for contacting portions of tooth structure, an open area 381 that provides access to portions of teeth for removal of tooth structure, a first base section 384, and a second base section 389.

The first base section 384 may include a first surface 386 facing in a direction opposite a working tooth 60 and a second surface 387 facing in a direction towards a working tooth 60 in which the first and second surfaces 386, 387 are separated by a thickness 388. The first base section 384 additionally may include a slot 385 having a length and a width.

As shown in FIG. 14, a receptacle 370 may be attached to the first base section 384 through the use of the slot 385. As in the receptacle 270 disclosed previously herein, the receptacle 370 may congruously surround a portion of a housing of a tooth treatment assembly, such as the housing of the tooth treatment assembly, when the housing is installed within the receptacle 370. The receptacle 370 preferably has a bottom base 323 from which a side wall 327 extends upwardly and around the periphery thereof leaving an opening 329 on one end. The opening 329 is large enough to accommodate the thickness of the connecting end of the hand grip. A combination of the bottom base 323 and the side wall 327 form inner and outer surfaces of the receptacle. The inner surface 373 of the receptacle 370 preferably conforms to the shape of a housing of the tooth treatment assembly, such as the housing of the tooth treatment assembly. The receptacle 370 may further have a head locking feature that is capable of engaging an undercut located on a housing of a tooth treatment assembly, such as the housing of the tooth treatment assembly, and a shaft locking feature that is capable of engaging an undercut located on a connecting end of a tooth treatment assembly, such as the connecting end of the tooth treatment assembly. A tool aperture 324 extends through the thickness of the bottom base 323 of the receptacle 370 to enable a tooth treatment element, such as tooth treatment element 252, as well as water jets or air streams to pass through.

The receptacle 370 may additionally include a guide plate 376 attached through a connecting portion to the bottom base 323. The guide plate 376 has a width. In a preferred arrangement, the width of the guide plate 376 is greater than the width of the slot 385 of the first base section 384. Further, the connection portion preferably has a length substantially equal to the thickness of the slot 385 and thus the guide plate 376 is preferably located such a distance from the bottom base 323. In this manner, when the guide plate 376 is inserted through the first surface 386 and then the thickness of the slot 385 of the first base section 384, the guide plate 376 is held substantially against the second surface 387 and thus limits the movement of the receptacle 370 in the direction towards the working tooth 60. Further, when the connecting portion attached to the guide plate 376 is inserted within the slot 385, the connecting portion of the receptacle 370 contacts the slot 385 to limit the lateral movement of the receptacle 370 with respect to the working tooth 60 being treated. Such a configuration thus limits the movement of a tooth treatment assembly adapted to fit within the receptacle 370 and a corresponding tooth treatment element with respect to the working tooth 60 being prepared.

In each of the embodiments presented herein, the overlay 290, 390 preferably should remain fixed and not move once it is placed around the working tooth 60. Moreover, the overlay 290, 390 should remain in a stable position even when a dental instrument intended for use with the overlay 290, 390 makes contact with it. The position of the overlay 290, 390 can be secured by contact of the contacting surfaces 282 of the overlay 290, 390 with tooth surfaces or by the use of a bonding agent, such as one that is light cured or a temporary cement or by projections from the overlay 290, 390 that engage portions of a tooth, including the working tooth 60, either of the adjacent teeth 65, or dentition on the opposing jaw.

It may be possible to utilize the same configuration of an overlay, such as the overlays 90, 290 described previously herein, made for one tooth, in the preparation of a tooth of the same or different patient, where such other tooth has sufficiently similar dimensions, shape and condition. Therefore, it is within the scope of this invention to have some overlays prepared which can be standardized, reused and/or reproduced. Also, it is within the scope of this invention to utilize data obtained in the preparation of prior overlays and restoration parts in the design and generation of new overlays having substantially similar dimensions and shapes.

A dentist may use a dental instrument such as the dental instrument 10 and an overlay configuration such as the overlay 90 previously described to remove portions of the structure of a working tooth with precision. It is generally preferred to retain and utilize as much of a healthy working tooth as practical. When a tooth is damaged or infected, the damaged and/or infected parts of the tooth may have to be removed first, and the tooth may have to be reconstructed before preparing the tooth for further treatment with a restoration device. The preliminary repair or reconstruction of the tooth minimizes the chance that an infection develops underneath a tooth restoration part. This also maximizes the lifetime of the tooth restoration part as the basis for the tooth restoration part, namely the working tooth, no longer contains defective or damaged portions.

Several methods are known for acquiring three-dimensional data from a patient's dentition to determine the portions of a tooth that should be removed based on factors of decay and structural defects, as well as portions of tooth that should be retained intact to provide sufficient strength in the ultimate preparation of a dental overlay configuration. Such data can be retrieved, for example, by processing and analyzing photographs, x-rays or other information taken from the patient's dentition or by directly obtaining such data from the patient through the use of intra-oral scanning devices. Another method is making a physical impression of the dentition and then subsequently scanning this impression or a reversed cast of the impression. Such scanning can be conducted with a CAD/CAM 3D scanning device. Illustrative of such a device is the Activity 101 Scanner from Smart Optics, DentalWings 3-Series Scanner, or 3Shape 710 Scanner of Woburn, Mass., USA. While such a scanning device can scan a model of the dental arch with a tolerance of about 10 µm this does not take into account other error factors obtained from the making of the impression and the casting of the dental impression. In preparing the ultimate restoration part or dental prosthesis, these other error factors or tolerances must be considered.

The CAD program can choose the specific configuration for the overlay, and ultimately the configuration for the prepared tooth by utilizing certain protocols which are based on prior experience for preparing dental prostheses.

After acquiring the three-dimensional data, this data can be processed by a computer so as to determine a portion of tooth structure to be removed from the tooth. The portion of the tooth to be removed will be determined in view of any further tooth treatment required. If a particular shape of the prepared tooth is required for allowing further treatment, the portion for tooth structure removal will be chosen so that after preparation of the tooth, this particular shape will remain.

Determining the portion for tooth structure removal depends on many parameters and will differ from case to case. Parameters include the location of the tooth in the mouth of the patient, amount and location of the damaged tooth structure, distance of the tooth to neighboring teeth, the bite of the patient, etc. In a preferred embodiment, the computer will also take into account the different parts of the tooth such as the enamel, dentin, pulp, cementum, etc. in determining the predetermined part. It is also understood within the general aspects of the invention that the patient's tooth may have to be built up through conventional techniques and materials prior to the actual step of preparation of the tooth, utilizing the overlay or after preparation if the decay is exposed.

According to the invention, the computer is programmed to automatically determine the predetermined part of tooth structure to be removed. However, also according to the invention, the computer can be programmed either by manually selecting parameters or actually inputting code to determine the portion for tooth structure removal subject to additional limitations or parameters imposed by a practitioner. The practitioner's input can be included by visualizing data relating to the tooth onto a computer display and allowing the practitioner to enter a parameter relating to the preparation of the tooth. Preferably, a preview of the tooth is visualized onto the computer display together with a preview of a simulation of the prepared tooth, so as to allow a practitioner to see the impact of chosen parameters onto the prepared tooth. The latter feature provides a larger degree of freedom to the dentist or practitioner to benefit from advice from other practitioners. The method for producing a dentist tool according to the invention enables a less experienced dentist to benefit from computer-assisted recommendations as well as other practitioners.

Next, the dental overlay is installed into the mouth of a patient in a manner to secure the overlay in a position to enable the overlay to limit a dentist's movement of a tooth treatment element of a dental instrument. A dental instrument is then employed into the mouth of a patient by orienting it in a manner such that guide projections extending from the dental instrument are situated between the guide surfaces of two or more guide walls that are arranged in a configuration for contacting the guide projections.

In one embodiment, a bottom surface of a projection head on a dental instrument can rest on a top surface of the guide walls. In this manner, the predetermined height of the guide walls determines the depth of penetration of a tooth treatment element on a dental instrument. When the top surfaces of the guide walls are substantially flat and a portion of a dental instrument such as a projection head is laid across these top surfaces, the dental instrument may be slid along these top surfaces.

Finally, the dentist's instrument may be operated in conjunction with the dental overlay. In this regard, when a tooth treatment element such as a dental bur extends from a dentist's instrument, sliding the dentist's instrument along the top surfaces will produce a predetermined depth or predetermined depths of cut within a prepared tooth 70, as shown in FIG. 10. Accordingly, the limitations of the guide surfaces of the guide walls in conjunction with the limits sets by the height of the guide walls upon a tooth treatment element of a dentist's instrument define a three-dimensional region of the working tooth in which portions of tooth structure are removed.

Although the invention herein has been described with reference to particular embodiments, in both described and illustrated contexts, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A dental overlay for temporary installation into the mouth of a patient to guide a dental instrument having a tooth treatment element configured for removing a portion of tooth structure from a tooth in the removal of a prede- termined portion of working tooth structure to be removed from a working tooth to be treated, the overlay comprising:
(i) a base having one or more surfaces for contacting portions of one or more teeth in a mouth of a patient to secure the overlay in a suitable position with respect to the tooth to be treated, and the base further having one or more open areas for exposing the portion of the working tooth structure to be removed; and
(ii) a cutting guide comprising a plurality of sets of adjacent guide walls extending from the base, each of the sets of adjacent guide walls defining, in combination with the base, a respective side aperture for receipt of a guide projection of separated guide projections of the dental instrument, a combination of a guide wall of each of the sets of adjacent guide walls and the base defining a side opening for receipt of the tooth treatment element through the side opening, wherein the side opening has a width as measured in a first plane perpendicular to the sets of adjacent guide walls that is larger than a width of each of the side apertures as measured in the first plane, and wherein the adjacent guide walls of each of the sets of adjacent guide walls have a predetermined configuration for contacting a guide projection of separated guide projections of the dental instrument to limit the movement of the tooth treatment element of the dental instrument without the tooth treatment element contacting the guide walls of the cutting guide and to restrict the portion of the working tooth structure to be removed to the predetermined portion of the working tooth to be treated.

2. The dental overlay of claim 1, wherein the adjacent guide walls have a predetermined height which can limit the movement of the tooth treatment element in the apical direction of the tooth.

3. The dental overlay of claim 1, wherein the adjacent guide walls within any one of the sets of adjacent guide walls are substantially parallel to each other along their entire lengths.

4. The dental overlay of claim 1, wherein the overlay is configured for limiting the movement of the dental instrument in the distal direction.

5. The dental overlay of claim 1, wherein the overlay is configured for limiting the movement of the dental instrument in a direction substantially parallel to the proximal surfaces of the tooth to be treated.

6. The dental overlay of claim 1, wherein the overlay is configured for preparing the working tooth to be treated to receive one or more of a crown, inlay, onlay, bridge, and veneer.

7. The dental overlay of claim 1, wherein the predetermined configuration of the cutting guide limits the movement of the tooth treatment element such that the portion of the working tooth structure removed from the working tooth includes tooth structure subject to a condition of chipping, cracking, decay and/or structural weakness.

8. A dental system, comprising:
the dental overlay of claim 1; and
a dental instrument for use with the dental overlay in guiding the dental instrument, the dental instrument comprising:
a hand grip;
a tooth treatment assembly including a tooth treatment element configured for removing a portion of tooth structure from a working tooth; and
a plurality of parallel guide projections extending from the tooth treatment assembly in the direction of the portion of the working tooth structure to be removed when the tooth treatment element is in position for working tooth structure removal, each of the plurality of guide projections being spaced from the tooth treatment element of the tooth treatment assembly and configured for receipt between and for contact with the adjacent guide walls of one of the sets of adjacent guide walls of the cutting guide of the overlay in the vicinity of the working tooth to limit three-dimensional movement of the tooth treatment element and to restrict the portion of the working tooth structure to be removed to the predetermined portion of the working tooth to be treated.

9. The dental system of claim 8, further comprising:
a projection head from which each guide projection extends, wherein the projection head is configured for resting on a portion of the cutting guide and each guide projection has a predetermined length to correspond with a portion of the cutting guide of the overlay.

10. The dental system of claim 8, wherein each guide projection is configured for contacting a portion of the cutting guide to limit lateral movement of the tooth treatment element with respect to the portion of the working tooth structure to be removed.

11. The dental system of claim 9, wherein the projection head further comprises one or more flanges extending from the projection head in a direction perpendicular to each guide projection, and wherein each guide projection extends from one of the flanges.

12. A method for treating a working tooth to be treated in a patient's mouth by removing predetermined portions of working tooth structure from the working tooth, the method comprising the steps of:
receiving a plurality of guide projections of a dental instrument through respective side apertures, each of the side apertures being defined by and extending between ends of adjacent guide walls of a plurality of sets of adjacent guide walls of a dental overlay extending from a base of the overlay, the base being mounted on the working tooth or another tooth in the patient's mouth;
receiving a tooth treatment element of the dental instrument for removal of a portion of a tooth's structure through a side opening defined by and extending between a guide wall of each of the sets of adjacent guide walls, the side opening having a width as measured in a first plane perpendicular to the sets of adjacent guide walls that is larger than a width of each of the side apertures as measured in the first plane, wherein the plurality of guide projections extend from the dental instrument in a direction towards the working tooth when the tooth treatment element is in operating position for removal of the portions of the working tooth structure of the working tooth;
moving the tooth treatment element of the dental instrument in a direction perpendicular to the direction towards the working tooth while maintaining the one or more guide projections between the set of the guide walls of the dental overlay, the dental overlay being configured to contact the one or more guide projections of the dental instrument to limit the movement of the tooth treatment element of the dental instrument and to restrict the portion of the working tooth structure to be removed from the working tooth to the predetermined portions of working tooth structure.

13. The method of claim 12, further comprising:
placing the one or more guide projections of the dental instrument between a second set of guide walls of a second dental overlay mounted on the working tooth or another tooth in the patient's mouth, the second dental overlay being configured differently than the dental overlay;

moving the dental instrument in a direction towards the working tooth while maintaining the one or more guide projections between the second set of the guide walls of the second dental overlay, the second dental overlay being configured to contact the one or more guide projections of the dental instrument to limit the movement of the tooth treatment element of the dental instrument and to restrict the portion of the working tooth structure to be removed from the working tooth to be treated to the predetermined portions of working tooth structure of the working tooth.

14. The method of claim 12, further comprising:
acquiring three-dimensional data for the working tooth to be treated; and
processing the three-dimensional data with a computer to define the portions of the working tooth structure to be removed from the working tooth.

15. The method of claim 14, wherein the acquired three-dimensional data comprises an exterior shape and size of the working tooth to be treated and an interior structure of the working tooth sufficient to detect decay, cracks and other weaknesses of the tooth.

16. The method of claim 12, wherein the dental overlay has surfaces for contacting portions of the working tooth to be treated or another tooth in the patient's mouth to enable the dental overlay to be secure in the patient's mouth in a suitable position during treatment of the working tooth.

17. The method of claim 12, wherein the side opening is a first side opening, and wherein the dental overlay further comprises a second side opening defined by the base and configured to receive the tooth treatment element.

18. The method of claim 12, wherein the set of guide walls of the dental overlay limit the movement of the tooth treatment element of the dental instrument to restrict a remaining portion of working tooth structure, after the portion of the working tooth structure to be removed from the working tooth to be treated is removed, to a structure that conforms to and engages with a predetermined restoration.

19. A dental overlay for temporary installation into the mouth of a patient to guide a dental instrument having a tooth treatment element configured for removing a portion of tooth structure from a tooth in the removal of a predetermined portion of working tooth structure to be removed from a working tooth to be treated, the overlay comprising:
(i) a base having one or more surfaces for contacting portions of one or more teeth in a mouth of a patient to secure the overlay in a suitable position with respect to the tooth to be treated, and the base further having one or more open areas for exposing the portion of the working tooth structure to be removed; and
(ii) a cutting guide comprising a plurality of sets of adjacent guide walls extending from the base, a combination of a guide wall of each of the sets of adjacent guide walls and the base defining a side opening for receipt of the tooth treatment element through the side opening, wherein the guide walls of each of the sets of adjacent guide walls have a predetermined configuration for contacting a guide projection of separated guide projections of the dental instrument to limit the movement of the tooth treatment element of the dental instrument and to restrict the portion of the working tooth structure to be removed to the predetermined portion of the working tooth to be treated, wherein at least one guide wall of the sets of adjacent guide walls extends over the one or more open areas.

* * * * *